(12) United States Patent
Lowe et al.

(10) Patent No.: US 9,862,759 B2
(45) Date of Patent: Jan. 9, 2018

(54) METHOD FOR GENERATING AND SCREENING AN ANTIBODY LIBRARY

(75) Inventors: Peter Lowe, Droisy (FR); Cédric Bes, Nantes (FR); Nicolas Boute, Cernex (FR)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 260 days.

(21) Appl. No.: 12/745,469

(22) PCT Filed: Dec. 4, 2008

(86) PCT No.: PCT/EP2008/066804
§ 371 (c)(1),
(2), (4) Date: Jul. 2, 2010

(87) PCT Pub. No.: WO2009/080461
PCT Pub. Date: Jul. 2, 2009

(65) Prior Publication Data
US 2011/0003705 A1  Jan. 6, 2011

(30) Foreign Application Priority Data

Dec. 4, 2007  (FR) .................................... 07 08444

(51) Int. Cl.
*C12Q 1/68* (2006.01)
*C07K 16/00* (2006.01)

(52) U.S. Cl.
CPC ................ *C07K 16/00* (2013.01); *C12Q 1/68* (2013.01); *C12Q 1/6844* (2013.01)

(58) Field of Classification Search
None
See application file for complete search history.

(56) References Cited

U.S. PATENT DOCUMENTS

| | | | |
|---|---|---|---|
| 6,635,424 B2 * | 10/2003 | Wigler et al. | 435/6.16 |
| 6,977,153 B2 * | 12/2005 | Kumar et al. | 435/6.12 |
| 7,405,062 B2 * | 7/2008 | Ji | 435/91.2 |
| 7,790,388 B2 | 9/2010 | Landegren et al. | |
| 2003/0049731 A1 * | 3/2003 | Bowdish | C07K 16/00 435/69.1 |
| 2004/0171041 A1 * | 9/2004 | Dahl et al. | 435/6 |

FOREIGN PATENT DOCUMENTS

| | | |
|---|---|---|
| WO | WO 01/79481 A2 | 10/2001 |
| WO | WO 03/012119 A2 | 2/2003 |
| WO | WO 03/054016 A2 | 7/2003 |
| WO | WO 2005/019270 A2 | 3/2005 |
| WO | WO 2006/063355 A2 | 6/2006 |
| WO | WO 2008/012529 A1 | 1/2008 |

OTHER PUBLICATIONS

Martin, TE. et al. A novel mitogenic protein that is highly expressed in cells of the gastric antrum mucosa. Am J Physiol., vol. 285, p. G332-G343, 2003.*
Sassano, M. et al. PCR amplification of antibody variable regions using primers that anneal to constant regions. Nucleic Acids Research, vol. 22, No. 9, p. 1768-1769, 1994.*
Jiang, Z. et al. Regulation of recombinant monoclonal antibody production in chinese hamster ovary cells: A comparative study of gene copy number, mRNA level, and protein expression. Biotechnol. Prog., vol. 22, p. 313-318, 2006.*
Polidoros, AN. et al. Rolling circle amplification-RACE: a method for simultaneous isolation of 5'and 3' cDNA ends from amplified cDNA templates. Biotechniques, vol. 41, p. 35-42, 2006.*
Christ et al., Tapping Diversity Lost in Transformations—in vitro Amplification of Ligation Reactions, Nucleic Acids Research, 2006, vol. 34, No. 16, pp. 1-6.
International Search Report for PCT/EP2008/066804 dated Mar. 5, 2009.
Kohler et al., "Continuous Cultures of Fused Cells Secreting Antibody of Predefined Specificity," Nature, vol. 256, Aug. 7, 1975, pp. 495-497.
Loh et al., "Polymerase Chain Reaction with Single-Sided Specificity: Analysis of T Cell Receptor δ Chain," Science, Jan. 13, 1989, pp. 217-220, XP000673517.
McCafferty et al., "Phage Antibodies: Filamentous Phase Displaying Antibody Variable Domains," Nature, vol. 348, Dec. 6, 1990, pp. 552-554.
Polidoros et al., "Rolling Circle Amplification-RACE: a Method for Simultaneous Isolation of 5' and 3' cDNA Ends From Amplified cDNA Templates," BioTechniques, vol. 41, No. 1, Jul. 2006, XP-002488782.
Polidoros et al., "Supplementary Material for: Rolling Circle Amplification-RACE: a Method for Simultaneous Isolation of 5' and 3' cDNA Ends From Amplified cDNA Templates," BioTechniques, vol. 41, No. 1, pp. 35, Jul. 2006.
Scott et al., "Searching for Peptide Ligends with an Epitope Library," Science, vol. 249, Jul. 27, 1990, pp. 386-390.
Smith, "Filamentous Fusion Phage: Novel Expression Vectors That Display Cloned Antigens on the Virion Surface," Science, vol. 228, Jun. 14, 1985, pp. 1315-1317.
Dean et al., "Rapid Amplification of Plasmid and Phage DNA using Phi29 DNA Polymerase and Multiply-Primed Rolling Circle Amplification", Genome Research, vol. 11, No. 6, (2001) pp. 1095-1099.
Frey et al., "Production of in vitro ampiified DNA pseudolibraries and high-throughput cDNA target amplifiation", BMC Biotechnology, vol, 7, No. 31 (2007) pp. 1-5.

\* cited by examiner

*Primary Examiner* — Prabha Chunduru
(74) *Attorney, Agent, or Firm* — Birch, Stewart, Kolasch & Birch, LLP

(57) ABSTRACT

The invention relates to a method for generating a DNA sequence coding for the heavy chain or the light chain of at least one antibody from RNA from a cell capable of producing an antibody. More particularly, the invention relates to the generation of a monoclonal antibody library. The invention also relates to the use of an antibody library for screening monoclonal antibodies, preferably human antibodies for treating cancer.

12 Claims, 12 Drawing Sheets

```
                          5'-GATAGACAGATGGGGGTGTCG-3'   (III)

5'-AGCAGACCCGGGGGCCAGTGGATAGACAG-3'                    (I)
     ||||||||||||||||||||||
   3'-CGTCTGGGCCCCCGGTCACC-5'                          (II)
```

FIG.4

```
                                  5'-GGTGGGAAGATGGATACAG-3'   (III)

5'-TCCAGATGTTAACTGCTCACTGGATGGTGGGAAGATGGATACAG-3'            (I)
      |||||||||||||||||||||
    3'-GGTCTACAATTGACGAGTG-5'                                 (II)
```

FIG.5

1    TCT AGA GGA TCC CCG GGT CTG CTA AAA ATA TGT CCA ATG TCC TCT CCA CAG

52   ACA CTG AAC ACA CTG ACT CTA ACC ATG GAA TGG AGC TGG ATC TTT CTC TTT
                                       M   E   W   S   W   I   F   L   F

103  CTC CTG TCA GGA ACT GCA GGT GTC CTC TCT GAG GTC CAG CTG CAA CAG TTT
      L   L   S   G   T   A   G   V   L   S   E   V   Q   L   Q   Q   F

154  GGA GCT GAG CTG GTG AAG CCT GGG GCT TCA GTG AAG ATA TCC TGC AAG GCT
      G   A   E   L   V   K   P   G   A   S   V   K   I   S   C   K   A

205  TCT GGC TAC ACA TTC ACT GAC TAC AAC ATG GAC TGG GTG AAG CAG AGC CAT
      S   G   Y   T   F   T   D   Y   N   M   D   W   V   K   Q   S   H

256  GGA AAG AGC CTT GAG TGG ATT GGA GAT ATT AAT CCT AAC TAT GAT CGT ACT
      G   K   S   L   E   W   I   G   D   I   N   P   N   Y   D   R   T

307  ACC TAC AAC CAG AAG TTC AAG GGA AAG GCC ACA TTG ACT GTA GAC AAG TCC
      T   Y   N   Q   K   F   K   G   K   A   T   L   T   V   D   K   S

358  TCC AGC ACA GCC TAC ATG GAG CTC CGC AGC CTG ACA TCT GAG GAC ACT GCA
      S   S   T   A   Y   M   E   L   R   S   L   T   S   E   D   T   A

409  GTC TAT TAC TGT GCA AGA AGG GAG ATT ACG ACG GAA TTT GAC TAC TGG GGC
      V   Y   Y   C   A   R   R   E   I   T   T   E   F   D   Y   W   G

460  CAA GGC ACC ACT CTC ACA GTC TCC TCA GCC AAA ACG ACA CCC CCA TCT GTC
      Q   G   T   T   L   T   V   S   S   A   K   T   T   P   P   S   V

511  TAT CCA CTG GCC CCC GGG ATA CCG AGC TCG A
      Y   P   L   A   P   G

FIG.6

```
                              <------------------------------------------- FR1 - IMGT
                              1              5             10                   15
IGHV1-18*01                   gag gtc cag ctg caa cag tct gga cct ... gag ctg gtg aag cct
Standard approach             --- --- --- --- --- --- -t- --- g-- ... --- --- --- --- ---
Inventive approach            --- --- --- --- --- --- -t- --- g-- ... --- --- --- --- ---

----------------------------------------->
                                            20              25                     30
IGHV1-18*01                   ggg gct tca gtg aag ata ccc tgc aag gct tct gga tac aca ttc
Standard approach             --- --- --- --- --- --- t-- --- --- --- --- --- --c --- ---
Inventive approach            --- --- --- --- --- --- t-- --- --- --- --- --- --c --- ---

CDR1 - IMGT                  <---------------------------
                                            35                    40                    45
IGHV1-18*01                   act gac tac aac ... ... ... ... atg gac tgg gtg aag cag agc
Standard approach             --- --- --- --- ... ... ... ... --- --- --- --- --- --- ---
Inventive approach            --- --- --- --- ... ... ... ... --- --- --- --- --- --- ---

FR2 - IMGT  ----------------------------->            CDR2
                                             50              55                     60
IGHV1-18*01                   cat gga aag agc ctt gag tgg att gga gat att aat cct aac aat
Standard approach             --- --- --- --- --- --- --- --- --- --- --- --- --- --- t--
Inventive approach            --- --- --- --- --- --- --- --- --- --- --- --- --- --- t--

- IMGT        <-----------------------------------------
                                             65              70                     75
IGHV1-18*01                   ggt ggt act ... ... atc tac aac cag aag ttc aag ... ggc aag
Standard approach             -a- c-- --- ... ... -c- --- --- --- --- --- --- ... --a ---
Inventive approach            -a- c-- --- ... ... -c- --- --- --- --- --- --- ... --a ---

-------------------------------- FR3 - IMGT ----------------
                                            80              85                    90
IGHV1-18*01                   gcc aca ttg act gta gac aag tcc tcc agc aca gcc tac atg gag
Standard approach             --- --- --- --- --- --- --- --- --- --- --- --- --- --- ---
Inventive approach            --- --- --- --- --- --- --- --- --- --- --- --- --- --- ---

------------------------------------------------------->
                                            95             100                    105
IGHV1-18*01                   ctc cgc agc ctg aca tct gag gac act gca gtc tat tac tgt gca
Standard approach             --- --- --- --- --- --- --- --- --- --- --- --- --- --- ---
Inventive approach            --- --- --- --- --- --- --- --- --- --- --- --- --- --- ---

CDR3 -   IMGT                 <--------------------
                                            110                    115                120
IGHV1-18*01                   aga
IGHD2-13*01                       atg gtg act ta
IGHJ2*01                                      ac tcc gaa ttt gac tac tgg ggc caa ggc acc
Standard approach             --- -g- -a- -t- acg a-g --- --- --- --- --- --- --- --- ---
Inventive approach            --- -g- -a- -t- acg a-g --- --- --- --- --- --- --- --- ---

FR4 - IMGT--------->
                                            125
IGHJ2*01                      act ctc aca gtc tcc tca
Constant domain gamma 1
Standard approach             --- --- --- --- --- ---
Inventive approach            --- --- --- --- --- ---
```

FIG.7

```
                    1               5                    10                       15
                    M   E   W   S   W   I   F   L   F   L   L   S   G   T   A
Genomic sequence    atg gaa tgg agc tgg atc ttt ctc ttt ctc ctg tca gga act gca
Standard approach   --- -g- --- --- g-- g-- --- a-- --- --- --- --- --- --- ---
Inventive approach  --- --- --- --- --- --- --- --- --- --- --- --- --- --- ---

21
                    G   V   L   S
Genomic sequence    ggt gtc ctc tct
Standard approach   --- --- --- ---
Inventive approach  --- --- --- ---
```

FIG.8

```
indirect   1   CGGCCGCACTAGTGATAACATCTTAAGCATCCTCTCTTCCAGCTCTCAGAGATGGAGACA
                                                                    M  E  T indirect  61   GACACACTCCTGCTATGGGTGCTGCTGCTCTGGGTTCCAGGTTCCACAGGTGACATTGTG
                D  T  L  L  W  V  L  L  L  W  V  P  G  S  T  G  D  I  V indirect 121   TTGACCCAATCTCCAGCTTCTTTGGCTGTGTCTCTAGGGCAGAGGGCCACCATATCCTGC
                L  T  Q  S  P  A  S  L  A  V  S  L  G  Q  R  A  T  I  S  C indirect 181   AGAGCCAGTGAAAATGTTGATAGTTATGGCAATAGTTTTATGCACTGGTATCAGCAGAAA
                R  A  S  E  N  V  D  S  Y  G  N  S  F  M  H  W  Y  Q  Q  K indirect 241   CCAGGACAGCCACCCAAACTCCTCATCTATCGTGCATCCAACCTAGAATCTGGGATCCCT
                P  G  Q  P  P  K  L  L  I  Y  R  A  S  N  L  E  S  G  I  P indirect 301   GCCAGGTTCAGTGGCAGTGGGTCTAGGACAGACTTCACCCTCACCATTAATCCTGTGGAG
                A  R  F  S  G  S  G  S  R  T  D  F  T  L  T  I  N  P  V  E indirect 361   GCTGATGATGTTGCAACCTATTACTGTCAACAAAGTAATGAGGATCCGTACACGTTCGGA
                A  D  D  V  A  T  Y  Y  C  Q  Q  S  N  E  D  P  Y  T  F  G indirect 421   GGGGGGACCAAGCTGGAAATAAAACGGGCTGATGCTGCACCAACTGTATCCATCTTCCCA
                G  G  T  K  L  E  I  K  R  A  D  A  A  P  T  V  S  I  F  P indirect 481   CCATCCAGTGAGCAGTTATCCCGCGGCCATGGCGGCCGGGAG
                P  S  S  E  Q  L  S  R  G  H  G  G  R  E
```

FIG.9

```
indirect    1  ACGCGTTTGTACAACATATGTCCAATGTCCTCTCCTCAGACACTGAACACACTGACTCTA indirect   61  ACCATGGGATGGAGCTGGATCTTTCTCTTTCTCCTGTCAGGAACTGCAGGTGTCCTCTCT
                 M  G  W  S  W  I  F  L  F  L  L  S  G  T  A  G  V  L  S indirect  121  GAGGTCCAGCTGCAACAGTCTGGACCTGAGCTGGTGAAGCCTGGGGCTTCAGTGAAGATA
                E  V  Q  L  Q  Q  S  G  P  E  L  V  K  P  G  A  S  V  K  I indirect  181  TCCTGCAAGACTTCTGGATACATATTCACTGCATACACCATGCACTGGGTGAGGCAGAGC
                S  C  K  T  S  G  Y  I  F  T  A  Y  T  M  H  W  V  R  Q  S indirect  241  CTTGGAGAGAGCCTTGACTGGATTGGAGGTATTAAACCAAACAATGGTCTTGCTAACTAC
                L  G  E  S  L  D  W  I  G  G  I  K  P  N  N  G  L  A  N  Y indirect  301  AACCAGAAGTTCAAGGGCAAGGCCACATTGACTGTAGACAAGTCCTCCAGCACAGCCTAC
                N  Q  K  F  K  G  K  A  T  L  T  V  D  K  S  S  S  T  A  Y indirect  361  ATGGACCTCCGCAGCCTGACATCTGAGGATTCTGCAGTCTATTACTGTGCAAGATCTGAG
                M  D  L  R  S  L  T  S  E  D  S  A  V  Y  Y  C  A  R  S  E indirect  421  ATTACGACGGAATTTGACTACTGGGGCCAAGGCACCGCTCTCACAGTCTCCTCAGCCAAA
                I  T  T  E  F  D  Y  W  G  Q  G  T  A  L  T  V  S  S  A  K indirect  481  ACGACACCCCCATCTGTCTATCCACTGGCCCCTGGATCTGCTGCCCAAACTAACTCCATG
                T  T  P  P  S  V  Y  P  L  A  P  G  S  A  A  Q  T  N  S  M indirect  541  GTGACCCTGGGATGCCTGGTCAAGGGCTATACGCGT
                V  T  L  G  C  L  V  K  G  Y  T  R
```

FIG.10

```
direct    1   ..CATATGTCCAATGTCCTCTCCTCAGACACTGAACACACTGACTCTAACCATGGGATGG
                                                              M  G  W direct   61   AGCTGGATCTTTCTCTTTCTCCTGTCAGGAACTGCAGGTGTCCTCTCTGAGGTCCAGCTG
               S  W  I  F  L  F  L  L  S  G  T  A  G  V  L  S  E  V  Q  L direct  121   CAACAGTCTGGACCTGAGCTGGTGAAGCCTGGGGCTTCAGTGAAGATATCCTGCAAGACT
               Q  Q  S  G  P  E  L  V  K  P  G  A  S  V  K  I  S  C  K  T direct  181   TCTGGATACATATTCACTGCATACACCATGCACTGGGTGAGGCAGAGCCTTGGAGAGAGC
               S  G  Y  I  F  T  A  Y  T  M  H  W  V  R  Q  S  L  G  E  S direct  241   CTTGACTGGATTGGAGGTATTAAACCAAACAATGGTCTTGCTAACTACAACCAGAAGTTC
               L  D  W  I  G  G  I  K  P  N  N  G  L  A  N  Y  N  Q  K  F direct  301   AAGGGCAAGGCCACATTGACTGTAGACAAGTCCTCCAGCACAGCCTACATGGACCTCCGC
               K  G  K  A  T  L  T  V  D  K  S  S  S  T  A  Y  M  D  L  R direct  361   AGCCTGACATCTGAGGATTCTGCAGTCTATTACTGTGCAAGATCTGAGATTACGACGGAA
               S  L  T  S  E  D  S  A  V  Y  Y  C  A  R  S  E  I  T  T  E direct  421   TTTGACTACTGGGGCCAAGGCACCGCTCTCACAGTCTCCTCAGCCAAAACGACACCCCCA
               F  D  Y  W  G  Q  G  T  A  L  T  V  S  S  A  K  T  T  P  P direct  481   TCTGTCTATCCACTGGCCCCTGGATCTGCTGCCCAAACTAACT
               S  V  Y  P  L  A  P  G  S  A  A  Q  T  N
```

FIG.11

```
combined    1                     ATATGTCCAATGTCCTCTCCTCAGACACTGAACACACTGACTCTA
indirect    1   ACGCGTTTGTACAACATATGTCCAATGTCCTCTCCTCAGACACTGAACACACTGACTCTA combined   46   ACCATGGGATGGAGCTGGATCTTTCTCTTTCTCCTGTCAGGAACTGCAGGTGTCCTCTCT
                  M  G  W  S  W  I  F  L  F  L  L  S  G  T  A  G  V  L  S
indirect   61   ACCATGGGATGGAGCTGGATCTTTCTCTTTCTCCTGTCAGGAACTGCAGGTGTCCTCTCT
                  M  G  W  S  W  I  F  L  F  L  L  S  G  T  A  G  V  L  S combined  106   GAGGTCCAGCTGCAACAGTCTGGACCTGAGCTGGTGAAGCCTGGGGCTTCAGTGAAGATA
                 E  V  Q  L  Q  Q  S  G  P  E  L  V  K  P  G  A  S  V  K  I
indirect  121   GAGGTCCAGCTGCAACAGTCTGGACCTGAGCTGGTGAAGCCTGGGGCTTCAGTGAAGATA
                 E  V  Q  L  Q  Q  S  G  P  E  L  V  K  P  G  A  S  V  K  I combined  166   TCCTGCAAGACTTCTGGATACATATTCACTGCATACACCATGCACTGGGTGAGGCAGAGC
                 S  C  K  T  S  G  Y  I  F  T  A  Y  T  M  H  W  V  R  Q  S
indirect  181   TCCTGCAAGACTTCTGGATACATATTCACTGCATACACCATGCACTGGGTGAGGCAGAGC
                 S  C  K  T  S  G  Y  I  F  T  A  Y  T  M  H  W  V  R  Q  S combined  226   CTTGGAGAGAGCCTTGACTGGATTGGAGGTATTAAACCAAACAATGGTCTTGCTAACTAC
                 L  G  E  S  L  D  W  I  G  G  I  K  P  N  N  G  L  A  N  Y
indirect  241   CTTGGAGAGAGCCTTGACTGGATTGGAGGTATTAAACCAAACAATGGTCTTGCTAACTAC
                 L  G  E  S  L  D  W  I  G  G  I  K  P  N  N  G  L  A  N  Y combined  286   AACCAGAAGTTCAAGGGCAAGGCCACATTGACTGTAGACAAGTCCTCCAGCACAGCCTAC
                 N  Q  K  F  K  G  K  A  T  L  T  V  D  K  S  S  S  T  A  Y
indirect  301   AACCAGAAGTTCAAGGGCAAGGCCACATTGACTGTAGACAAGTCCTCCAGCACAGCCTAC
                 N  Q  K  F  K  G  K  A  T  L  T  V  D  K  S  S  S  T  A  Y combined  346   ATGGACCTCCGCAGCCTGACATCTGAGGATTCTGCAGTCTATTACTGTGCAAGATCTGAG
                 M  D  L  R  S  L  T  S  E  D  S  A  V  Y  Y  C  A  R  S  E
indirect  361   ATGGACCTCCGCAGCCTGACATCTGAGGATTCTGCAGTCTATTACTGTGCAAGATCTGAG
                 M  D  L  R  S  L  T  S  E  D  S  A  V  Y  Y  C  A  R  S  E combined  406   ATTACGACGGAATTTGACTACTGGGGCCAAGGCACCGCTCTCACAGTCTCCTCAGCCAAA
                 I  T  T  E  F  D  Y  W  G  Q  G  T  A  L  T  V  S  S  A  K
indirect  421   ATTACGACGGAATTTGACTACTGGGGCCAAGGCACCGCTCTCACAGTCTCCTCAGCCAAA
                 I  T  T  E  F  D  Y  W  G  Q  G  T  A  L  T  V  S  S  A  K combined  466   ACGACACCCCCATCTGTCTATCCACTGGCCCCTGGATCTGCTGCCCAAACTAACT
                 T  T  P  P  S  V  Y  P  L  A  P  G  S  A  A  Q  T  N
indirect  481   ACGACACCCCCATCTGTCTATCCACTGGCCCCTGGATCTGCTGCCCAAACTAACTCCATG
                 T  T  P  P  S  V  Y  P  L  A  P  G  S  A  A  Q  T  N  S  M indirect  541   GTGACCCTGGGATGCCTGGTCAAGGGCTATACGCGT
                 V  T  L  G  C  L  V  K  G  Y  T  R
```

FIG.12

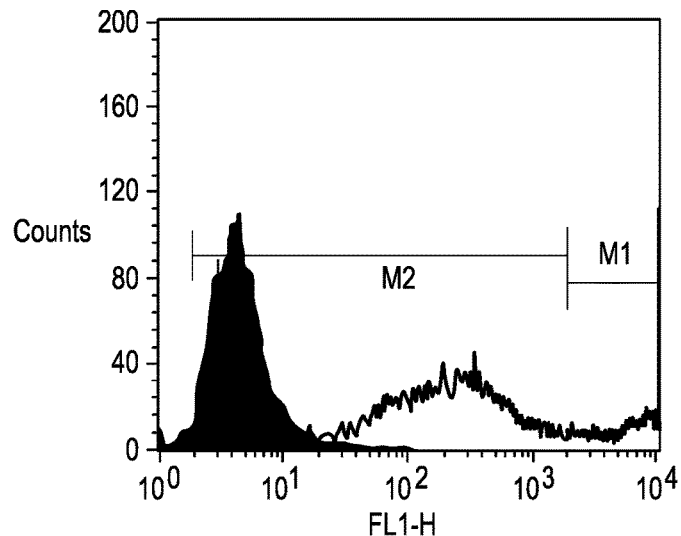
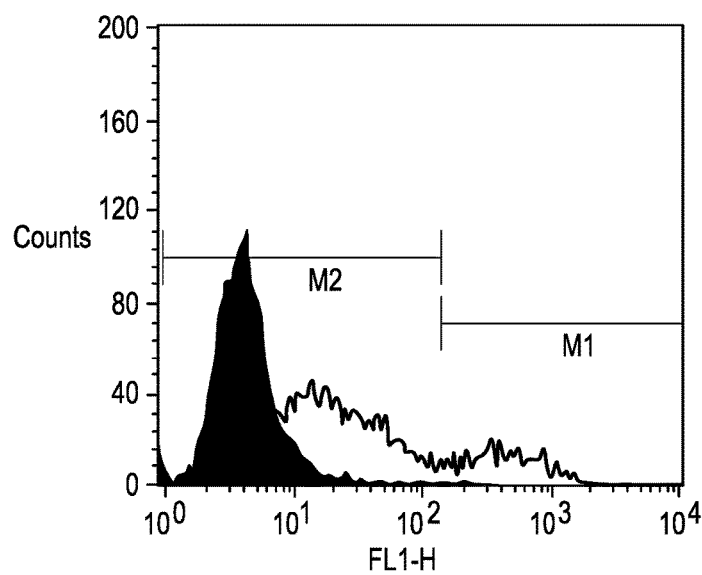
FIG.14

```
                        5'-GCCCTGGGCTGCCTGGTC-3'      (II)
5'-CCACCAAGGGCCCATCNNNNN---NNNN GCCCTGGGCTGCCTGGTCAAGGACTACTTCCC-3'
                                ||||||||||||||||||
                            3'-GGACCCGACGGACCAGTTTGCGCA-5' (I, Mlu I)
                            3'-GGACCCGACGGACCAGTTAAC-5'   (I, Mfe I)
3'-GGTGGTTCCCGGGTAG-5'(III)
```

FIG.15A

```
                         5'-CATCTGATGAGCAGTTGAAATCTGG-3' (II)
5'-CTGCACCATCTGTCTTCATCTTCCCGCCATCTGATGAGCAGTTGAAATCTGGAACTGCCTCTGTTGTGTGCC-3'
                                  ||||||||||||||||||||||||
                              3'-GGTAGACTACTCGTCAACTTTAGACTGCGCA-5' (I, Mlu I)
  3'-CGTGGTAGACAGAAGTAGAAGG-5'(III)
```

FIG.15B

```
                           5'-CAAGCCAACAAGGCCACAC-3'(II)
5'-GTCACTCTGTTCCCRCCCTCCTCTGAGGAGCTYCAAGCCAACAAGGCCACACTRGTGTGYCT-3'
                                      |||||||||||||||||||
                                3'-GTTCGGTTGTTCCGGTGTGATGCGCA-5'(I, Mlu I)
3'-CAGTGAGACAAGGGYGGGAGG-5'(III)
```

FIG.15C

SEQUENCE LISTING

```
<160> NUMBER OF SEQ ID NOS: 51

<210> SEQ ID NO 1
<211> LENGTH: 29
<212> TYPE: DNA
<213> ORGANISM: Artificial Sequence
<220> FEATURE:
<223> OTHER INFORMATION: Heavy chain primer I

<400> SEQUENCE: 1
agcagacccg ggggccagtg gatagacag                              29

<210> SEQ ID NO 2
<211> LENGTH: 44
<212> TYPE: DNA
<213> ORGANISM: Artificial Sequence
<220> FEATURE:
<223> OTHER INFORMATION: Light chain primer I

<400> SEQUENCE: 2
tccagatgtt aactgctcac tggatggtgg gaagatggat acag              44

<210> SEQ ID NO 3
<211> LENGTH: 20
<212> TYPE: DNA
<213> ORGANISM: Artificial Sequence
<220> FEATURE:
<223> OTHER INFORMATION: Heavy chain primer II

<400> SEQUENCE: 3
cgtctgggcc cccggtcacc                                        20
```

<210> SEQ ID NO 4
<211> LENGTH: 19
<212> TYPE: DNA
<213> ORGANISM: Artificial Sequence
<220> FEATURE:
<223> OTHER INFORMATION: Light chain primer II

<400> SEQUENCE: 4
ggtctacaat tgacgagtg                                                19

<210> SEQ ID NO 5
<211> LENGTH: 21
<212> TYPE: DNA
<213> ORGANISM: Artificial Sequence
<220> FEATURE:
<223> OTHER INFORMATION: Heavy chain primer III

<400> SEQUENCE: 5
gatagacaga tgggggtgtc g                                             21

<210> SEQ ID NO 6
<211> LENGTH: 19
<212> TYPE: DNA
<213> ORGANISM: Artificial Sequence
<220> FEATURE:
<223> OTHER INFORMATION: Light chain primer III

<400> SEQUENCE: 6
ggtgggaaga tggatacag                                                19

<210> SEQ ID NO 7
<211> LENGTH: 411
<212> TYPE: DNA
<213> ORGANISM: Artificial Sequence
<220> FEATURE:
<223> OTHER INFORMATION: Heavy chain variable domain (according to the
      invention)

<400> SEQUENCE: 7
atggaatgga gctggatctt tctctttctc ctgtcaggaa ctgcaggtgt cctctctgag    60
gtccagctgc aacagtttgg agctgagctg gtgaagcctg ggcttcagt gaagatatcc    120 tgcaaggctt ctggctacac attcactgac tacaacatgg actgggtgaa gcagagccat   180
ggaaagagcc ttgagtggat tggagatatt aatcctaact atgatcgtac tacctacaac   240
cagaagttca gggaaaggc cacattgact gtagacaagt cctccagcac agcctacatg    300
gagctccgca gcctgacatc tgaggacact gcagtctatt actgtgcaag aagggagatt   360
acgacggaat ttgactactg gggccaaggc accactctca cagtctcctc a            411

<210> SEQ ID NO 8
<211> LENGTH: 411
<212> TYPE: DNA
<213> ORGANISM: Artificial Sequence
<220> FEATURE:
<223> OTHER INFORMATION: Heavy chain variable domain (classical
      approach)

<400> SEQUENCE: 8
atgggatgga gcggggtctt tatctttctc ctgtcaggaa ctgcaggtgt cctctctgag    60
gtccagctgc aacagtttgg agctgagctg gtgaagcctg ggcttcagt gaagatatcc    120 tgcaaggctt ctggctacac attcactgac tacaacatgg actgggtgaa gcagagccat   180
ggaaagagcc ttgagtggat tggagatatt aatcctaact atgatcgtac tacctacaac   240

```
cagaagttca agggaaaggc cacattgact gtagacaagt cctccagcac agcctacatg        300
gagctccgca gcctgacatc tgaggacact gcagtctatt actgtgcaag aagggagatt        360
acgacggaat tgactactg gggccaaggc accactctca cagtctcctc a                  411
```

<210> SEQ ID NO 9
<211> LENGTH: 57
<212> TYPE: DNA
<213> ORGANISM: Artificial Sequence
<220> FEATURE:
<223> OTHER INFORMATION: Nucleic sequence encoding the signal peptide of
      the heavy chain (according to the invention)

<400> SEQUENCE: 9

```
atggaatgga gctggatctt tctctttctc ctgtcaggaa ctgcaggtgt cctctct          57
```

<210> SEQ ID NO 10
<211> LENGTH: 57
<212> TYPE: DNA
<213> ORGANISM: Artificial Sequence
<220> FEATURE:
<223> OTHER INFORMATION: Nucleic sequence encoding the signal peptide of
      the heavy chain (classical approach)

<400> SEQUENCE: 10

```
atgggatgga gcggggtctt tatctttctc ctgtcaggaa ctgcaggtgt cctctct          57
```

<210> SEQ ID NO 11
<211> LENGTH: 541
<212> TYPE: DNA
<213> ORGANISM: Artificial Sequence
<220> FEATURE:
<223> OTHER INFORMATION: Nucleic sequence encoding the whole heavy chain

<400> SEQUENCE: 11

```
tctagaggat ccccgggtct gctaaaaata tgtccaatgt cctctccaca gacactgaac        60
acactgactc taaccatgga atggagctgg atctttctct ttctcctgtc aggaactgca       120
ggtgtcctct ctgaggtcca gctgcaacag tttggagctg agctggtgaa gcctggggct       180
tcagtgaaga tatcctgcaa ggcttctggc tacacattca ctgactacaa catggactgg       240
gtgaagcaga gccatggaaa gagccttgag tggattggag atattaatcc taactatgat       300
cgtactacct acaaccagaa gttcaaggga aaggccacat tgactgtaga caagtcctcc       360
agcacagcct acatggagct ccgcagcctg acatctgagg acactgcagt ctattactgt       420
gcaagaaggg agattacgac ggaatttgac tactggggcc aaggcaccac tctcacagtc       480
tcctcagcca aaacgacacc cccatctgtc tatccactgg ccccgggat accgagctcg       540 a                                                                       541
```

<210> SEQ ID NO 12
<211> LENGTH: 522
<212> TYPE: DNA
<213> ORGANISM: Artificial Sequence
<220> FEATURE:
<223> OTHER INFORMATION: Sequence encoding the whole light chain
      (according to the invention)

<400> SEQUENCE: 12

```
cggccgcact agtgataaca tcttaagcat cctctcttcc agctctcaga gatggagaca        60
gacacactcc tgctatgggt gctgctgctc tgggttccag gttccacagg tgacattgtg       120
ttgacccaat ctccagcttc tttggctgtg tctctagggc agagggccac catatcctgc       180
```

```
agagccagtg aaaatgttga tagttatggc aatagtttta tgcactggta tcagcagaaa      240
ccaggacagc acccaaact cctcatctat cgtgcatcca acctagaatc tgggatccct      300
gccaggttca gtggcagtgg gtctaggaca gacttcaccc tcaccattaa tcctgtggag     360
gctgatgatg ttgcaaccta ttactgtcaa caaagtaatg aggatccgta cacgttcgga    420 gggggggacca agctggaaat aaaacgggct gatgctgcac caactgtatc catcttccca   480
ccatccagtg agcagttatc ccgcggccat ggcggccggg ag                        522
```

<210> SEQ ID NO 13  
<211> LENGTH: 333  
<212> TYPE: DNA  
<213> ORGANISM: Artificial Sequence  
<220> FEATURE:  
<223> OTHER INFORMATION: Light chain variable domain (according to the invention)

<400> SEQUENCE: 13

```
gacattgtgt tgacccaatc tccagcttct ttggctgtgt ctctagggca gagggccacc     60
atatcctgca gagccagtga aaatgttgat agttatggca atagtttttat gcactggtat   120 cagcagaaac caggacagcc acccaaactc ctcatctatc gtgcatccaa cctagaatct   180
gggatccctg ccaggttcag tggcagtggg tctaggacag acttcaccct caccattaat   240
cctgtggagg ctgatgatgt tgcaacctat tactgtcaac aaagtaatga ggatccgtac   300
acgttcggag gggggaccaa gctggaaata aaa                                  333
```

<210> SEQ ID NO 14  
<211> LENGTH: 31  
<212> TYPE: DNA  
<213> ORGANISM: Artificial Sequence  
<220> FEATURE:  
<223> OTHER INFORMATION: Heavy chain primary primer

<400> SEQUENCE: 14

```
acaaacgcgt atagcccttg accaggcatc c                                    31
```

<210> SEQ ID NO 15  
<211> LENGTH: 30  
<212> TYPE: DNA  
<213> ORGANISM: Artificial Sequence  
<220> FEATURE:  
<223> OTHER INFORMATION: Light chain primary primer

<400> SEQUENCE: 15

```
acaaacgcgt tggtgggaag atggatacag                                       30
```

<210> SEQ ID NO 16  
<211> LENGTH: 20  
<212> TYPE: DNA  
<213> ORGANISM: Artificial Sequence  
<220> FEATURE:  
<223> OTHER INFORMATION: Heavy chain secondary primer

<400> SEQUENCE: 16

```
ctaactccat ggtgaccctg                                                  20
```

<210> SEQ ID NO 17  
<211> LENGTH: 19  
<212> TYPE: DNA  
<213> ORGANISM: Artificial Sequence  
<220> FEATURE:  
<223> OTHER INFORMATION: Light chain secondary primer -continued

<400> SEQUENCE: 17
gggctgatgc tgcaccaac					19

<210> SEQ ID NO 18
<211> LENGTH: 576
<212> TYPE: DNA
<213> ORGANISM: Artificial Sequence
<220> FEATURE:
<223> OTHER INFORMATION: Sequence encoding the whole heavy chain
      (according to the invention)

<400> SEQUENCE: 18
acgcgtttgt acaacatatg tccaatgtcc tctcctcaga cactgaacac actgactcta		60 accatgggat ggagctggat ctttctcttt ctcctgtcag gaactgcagg tgtcctctct		120 gaggtccagc tgcaacagtc tggacctgag ctggtgaagc ctggggcttc agtgaagata		180 tcctgcaaga cttctggata catattcact gcatacacca tgcactgggt gaggcagagc		240 cttggagaga gccttgactg gattggaggt attaaaccaa acaatggtct tgctaactac		300 aaccagaagt tcaagggcaa ggccacattg actgtagaca gtcctccag cacagcctac		360 atggacctcc gcagcctgac atctgaggat tctgcagtct attactgtgc aagatctgag		420 attacgacgg aatttgacta ctggggccaa ggcaccgctc tcacagtctc ctcagccaaa		480 acgacacccc catctgtcta tccactggcc cctggatctg ctgcccaaac taactccatg		540 gtgaccctgg gatgcctggt caagggctat acgcgt		576

<210> SEQ ID NO 19
<211> LENGTH: 354
<212> TYPE: DNA
<213> ORGANISM: Artificial Sequence
<220> FEATURE:
<223> OTHER INFORMATION: Heavy chain variable domain (according to the
      invention)

<400> SEQUENCE: 19
gaggtccagc tgcaacagtc tggacctgag ctggtgaagc ctggggcttc agtgaagata		60 tcctgcaaga cttctggata catattcact gcatacacca tgcactgggt gaggcagagc		120 cttggagaga gccttgactg gattggaggt attaaaccaa acaatggtct tgctaactac		180 aaccagaagt tcaagggcaa ggccacattg actgtagaca gtcctccag cacagcctac		240 atggacctcc gcagcctgac atctgaggat tctgcagtct attactgtgc aagatctgag		300 attacgacgg aatttgacta ctggggccaa ggcaccgctc tcacagtctc ctca		354

<210> SEQ ID NO 20
<211> LENGTH: 521
<212> TYPE: DNA
<213> ORGANISM: Artificial Sequence
<220> FEATURE:
<223> OTHER INFORMATION: Sequence encoding the whole heavy chain
      (according to the invention)

<400> SEQUENCE: 20
catatgtcca atgtcctctc ctcagacact gaacacactg actctaacca tgggatggag		60 ctggatcttt ctctttctcc tgtcaggaac tgcaggtgtc ctctctgagg tccagctgca		120 acagtctgga cctgagctgg tgaagcctgg gcttcagtg aagatatcct gcaagacttc		180 tggatacata ttcactgcat acaccatgca ctgggtgagg cagagccttg agagagcct		240 tgactggatt ggaggtatta aaccaaacaa tggtcttgct aactacaacc agaagttcaa		300

```
gggcaaggcc acattgactg tagacaagtc ctccagcaca gcctacatgg acctccgcag    360
cctgacatct gaggattctg cagtctatta ctgtgcaaga tctgagatta cgacggaatt    420
tgactactgg ggccaaggca ccgctctcac agtctcctca gccaaaacga caccccatc     480 tgtctatcca ctggcccctg gatctgctgc ccaaactaac t                        521
```

<210> SEQ ID NO 21
<211> LENGTH: 354
<212> TYPE: DNA
<213> ORGANISM: Artificial Sequence
<220> FEATURE:
<223> OTHER INFORMATION: Heavy chain variable domain (according to the invention)

<400> SEQUENCE: 21

```
gaggtccagc tgcaacagtc tggacctgag ctggtgaagc ctggggcttc agtgaagata    60
tcctgcaaga cttctggata catattcact gcatacacca tgcactgggt gaggcagagc    120
cttggagaga gccttgactg gattggaggt attaaaccaa acaatggtct tgctaactac    180
aaccagaagt tcaagggcaa ggccacattg actgtagaca gtcctccag cacagcctac     240 atggacctcc gcagcctgac atctgaggat tctgcagtct attactgtgc aagatctgag    300
attacgacgg aatttgacta ctggggccaa ggcaccgctc tcacagtctc ctca          354
```

<210> SEQ ID NO 22
<211> LENGTH: 31
<212> TYPE: DNA
<213> ORGANISM: Artificial Sequence
<220> FEATURE:
<223> OTHER INFORMATION: murine primary primer

<400> SEQUENCE: 22

```
acaaacgcgt ataaccttg accaggcatc c                                   31
```

<210> SEQ ID NO 23
<211> LENGTH: 30
<212> TYPE: DNA
<213> ORGANISM: Artificial Sequence
<220> FEATURE:
<223> OTHER INFORMATION: Murine primary primer

<400> SEQUENCE: 23

```
acaaacgcgt cagggatcca gagttccaag                                    30
```

<210> SEQ ID NO 24
<211> LENGTH: 31
<212> TYPE: DNA
<213> ORGANISM: Artificial Sequence
<220> FEATURE:
<223> OTHER INFORMATION: Murine primary primer

<400> SEQUENCE: 24

```
acaaacgcgt gtagcctttg acaaggcatc c                                  31
```

<210> SEQ ID NO 25
<211> LENGTH: 19
<212> TYPE: DNA
<213> ORGANISM: Artificial Sequence
<220> FEATURE:
<223> OTHER INFORMATION: Murine secondary primer

<400> SEQUENCE: 25

```
actggctcct cggtgactc                                                19
```

<210> SEQ ID NO 26
<211> LENGTH: 21
<212> TYPE: DNA
<213> ORGANISM: Artificial Sequence
<220> FEATURE:
<223> OTHER INFORMATION: Murine secondary primer

<400> SEQUENCE: 26
agtgactgtg acttggaact c                                             21

<210> SEQ ID NO 27
<211> LENGTH: 19
<212> TYPE: DNA
<213> ORGANISM: Artificial Sequence
<220> FEATURE:
<223> OTHER INFORMATION: Murine secondary primer

<400> SEQUENCE: 27
gtctatccac tggcccctg                                                19

<210> SEQ ID NO 28
<211> LENGTH: 20
<212> TYPE: DNA
<213> ORGANISM: Artificial Sequence
<220> FEATURE:
<223> OTHER INFORMATION: Murine secondary primer

<400> SEQUENCE: 28
ctggatcctc ggtgacactg                                               20

<210> SEQ ID NO 29
<211> LENGTH: 18
<212> TYPE: DNA
<213> ORGANISM: Artificial Sequence
<220> FEATURE:
<223> OTHER INFORMATION: Murine tertiary primer

<400> SEQUENCE: 29
gatagaccga tggggctg                                                 18

<210> SEQ ID NO 30
<211> LENGTH: 21
<212> TYPE: DNA
<213> ORGANISM: Artificial Sequence
<220> FEATURE:
<223> OTHER INFORMATION: Murine tertiary primer

<400> SEQUENCE: 30
gatagactga tggggtgtt g                                              21

<210> SEQ ID NO 31
<211> LENGTH: 18
<212> TYPE: DNA
<213> ORGANISM: Artificial Sequence
<220> FEATURE:
<223> OTHER INFORMATION: Murine tertiary primer

<400> SEQUENCE: 31
gatagacaga tggggctg                                                 18

<210> SEQ ID NO 32
<211> LENGTH: 24
<212> TYPE: DNA
<213> ORGANISM: Artificial Sequence
<220> FEATURE:

<223> OTHER INFORMATION: Human primary primer

<400> SEQUENCE: 32
acgcgtttga ccaggcagcc cagg                                              24

<210> SEQ ID NO 33
<211> LENGTH: 31
<212> TYPE: DNA
<213> ORGANISM: Artificial Sequence
<220> FEATURE:
<223> OTHER INFORMATION: Human primary primer

<400> SEQUENCE: 33
acgcgtcaga tttcaactgc tcatcagatg g                                      31

<210> SEQ ID NO 34
<211> LENGTH: 26
<212> TYPE: DNA
<213> ORGANISM: Artificial Sequence
<220> FEATURE:
<223> OTHER INFORMATION: Human primary primer

<400> SEQUENCE: 34
acgcgtagtg tggccttgtt ggcttg                                            26

<210> SEQ ID NO 35
<211> LENGTH: 18
<212> TYPE: DNA
<213> ORGANISM: Artificial Sequence
<220> FEATURE:
<223> OTHER INFORMATION: Human secondary primer

<400> SEQUENCE: 35
gccctgggct gcctggtc                                                     18

<210> SEQ ID NO 36
<211> LENGTH: 25
<212> TYPE: DNA
<213> ORGANISM: Artificial Sequence
<220> FEATURE:
<223> OTHER INFORMATION: Human secondary primer

<400> SEQUENCE: 36
catctgatga gcagttgaaa tctgg                                             25

<210> SEQ ID NO 37
<211> LENGTH: 19
<212> TYPE: DNA
<213> ORGANISM: Artificial Sequence
<220> FEATURE:
<223> OTHER INFORMATION: Human secondary primer

<400> SEQUENCE: 37
caagccaaca aggccacac                                                    19

<210> SEQ ID NO 38
<211> LENGTH: 16
<212> TYPE: DNA
<213> ORGANISM: Artificial Sequence
<220> FEATURE:
<223> OTHER INFORMATION: Human tertiary primer

<400> SEQUENCE: 38
gatgggccct tggtgg                                                       16

```
<210> SEQ ID NO 39
<211> LENGTH: 22
<212> TYPE: DNA
<213> ORGANISM: Artificial Sequence
<220> FEATURE:
<223> OTHER INFORMATION: Human tertiary primer

<400> SEQUENCE: 39
ggaagatgaa gacagatggt gc                                          22

<210> SEQ ID NO 40
<211> LENGTH: 21
<212> TYPE: DNA
<213> ORGANISM: Artificial Sequence
<220> FEATURE:
<223> OTHER INFORMATION: Human tertiary primer

<400> SEQUENCE: 40
ggagggyggg aacagagtga c                                           21

<210> SEQ ID NO 41
<211> LENGTH: 19
<212> TYPE: DNA
<213> ORGANISM: Artificial Sequence
<220> FEATURE:
<223> OTHER INFORMATION: Murine tertiary primer

<400> SEQUENCE: 41
cagttggtgc agcatcagc                                              19

<210> SEQ ID NO 42
<211> LENGTH: 57
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (17)..(25)
<223> OTHER INFORMATION: n is a, c, g, or t

<400> SEQUENCE: 42
ccaccaaggg cccatcnnnn nnnnngccct gggctgcctg gtcaaggact acttccc    57

<210> SEQ ID NO 43
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 43
acgcgtttga ccaggcagcc cagg                                        24

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44
caattgacca ggcagcccag g                                           21

<210> SEQ ID NO 45
<211> LENGTH: 16
<212> TYPE: DNA
```

```
<213> ORGANISM: Artificial Sequence
<220> FEATURE:
<223> OTHER INFORMATION: Synthetic oligonucleotide

<400> SEQUENCE: 45
gatgggccct tggtgg                                                      16

<210> SEQ ID NO 46
<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 46
ctgcaccatc tgtcttcatc ttcccgccat ctgatgagca gttgaaatct ggaactgcct      60
ctgttgtgtg cc                                                          72

<210> SEQ ID NO 47
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 47
acgcgtcaga tttcaactgc tcatcagatg g                                     31

<210> SEQ ID NO 48
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 48
ggaagatgaa gacagatggt gc                                               22

<210> SEQ ID NO 49
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 49
gtcactctgt tcccrccctc ctctgaggag ctycaagcca acaaggccac actrgtgtgy      60
ct                                                                     62

<210> SEQ ID NO 50
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 50
acgcgtagtg tggccttgtt ggcttg                                           26

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide
```

-continued

```
<220> FEATURE:
<221> NAME/KEY: misc_feature
<222> LOCATION: (7)..(7)
<223> OTHER INFORMATION: n is a, c, g, or t

<400> SEQUENCE: 51
ggagggnggg aacagagtga c                                              21
```

METHOD FOR GENERATING AND SCREENING AN ANTIBODY LIBRARY

The present invention relates to the field of monoclonal antibodies, among others human antibodies. More particularly, the present invention is directed to a novel method for generating a DNA sequence coding for a heavy chain and/or a light chain of at least one antibody, preferably from total or messenger RNA from a cell capable of expressing an antibody. The invention also comprises a method for generating a bank or library of antibodies, preferentially human antibodies, applying the steps of the previous method.

The expressions <<bank(s)>> or <<library(ies)>> will be indifferently used in the present description, both of these expressions having the same meaning.

Traditionally, monoclonal antibodies or fragments thereof were prepared by using the standard technique of hybridomas described by Kohler and Milstein (Kohler and Milstein, 1975, Nature 256, 495), the thereby obtained antibodies being then humanized.

More recently, novel methods, based on the understanding of natural mechanisms and on the development of DNA recombination techniques, have been developed for generating and expressing human monoclonal antibodies. In particular, the techniques aiming at obtaining combinatorial libraries, or banks of antibodies have been the subject of many developments. Such techniques in addition to the fact of being more rapid and with which it is possible to do without humanization steps, provide a more efficient use of the whole and of the variability of the list of antibodies.

Antibodies are glycoproteins of the superfamily of immunoglobulins formed with 4 polypeptide chains: 2 heavy chains (H for heavy) and 2 light chains (L for light) which are connected to each other by a variable number of disulfide bridges providing flexibility to the molecule. These chains form a Y-shaped structure and consist of immunoglobulin domains of about 110 amino acids. Each light chain consists of a constant region and of a variable region while the heavy chains consist of a variable region and of 3 or 4 constant regions depending on the isotype.

For a given antibody, the two heavy chains are identical, the same applies for the two light chains.

The constant regions are characterized by amino acid sequences which are very closely related from one antibody to the other, and are characteristics of the species and of the isotype. Each light chain has one exemplary thereof noted as $C_L$. The heavy chains include three or four constant regions $C_H1$, $C_H2$, $C_H3$ and $C_H4$ depending on the isotype.

An antibody has four variable regions located at the ends of the two <<arms>>. The association between a variable region borne by a heavy chain ($V_H$) and the adjacent variable region borne by a light chain ($V_L$) forms the recognition site (or paratope) of the antigen. Thus, an immunoglobulin molecule has two sites for binding to the antigen, one at the end of each arm. Both of these sites are identical, hence the possibility of binding two antigen molecules per antibody.

For heavy chains, the variable regions $V_H$ are coded by genes which include three types of segments, i.e. a variability segment (v segment or gene), a diversity segment (d segment or gene) and a junction segment (j segment or gene). The genes coding for the variable regions of the light chain $V_L$ also have a gene v and a gene j, but no gene d.

Initially, the naive immunity repertoire is derived from the combinatorial rearrangement of different genes coding for the variable regions. More particularly, the genes v, d, j for the heavy chain and v, j for the light chain, may be associated with each other independently, which explains the large diversity of the variable regions which may be generated. This first mechanism by which a very large number of functional units of different structures may be produced, is called combinatorial diversity.

Two other mechanisms will increase this diversity, one occurring in the initial step of differentiation of B lymphocytes (junctional diversity) and the other one during the immune response induced by antigenic stimulation (somatic hypermutations).

Junctional diversity is based on the appearance of mutations during the combinatorial rearrangement at junctions between the genes v-d and d-j for the heavy chain and v-j for the light chain.

A maturation of the affinity of the antibodies is carried out by a process for selecting somatic hypermutations which consist in point-like mutations exclusively occurring in the regions coding for the regions $V_H$ and $V_L$ and which may be the origin of changes in the structure of the paratope.

Diversity is therefore based on the three described elements, i.e. combinatorial diversity, junctional diversity and somatic hypermutations.

Starting with these elements, different technologies have been developed in order to be able to rapidly generate a large diversity of human antibodies and have proved to be particularly interesting in the case of human antibodies for which the hybridomas are technically difficult to obtain.

More particularly, the advent of the so-called <<phage display>> technology (Smith, 1985, Science, 228:1315; Scott & Smith, 1990 Science, 249:386; McCafferty, 1990, Nature, 348:552) has given the possibility of selecting in vitro, from libraries, antibodies or fragments of human antibodies directed against a large variety of targets, or antigens. These libraries are divided into two groups, i.e. natural libraries and synthetic libraries.

Natural libraries are built from genes directly recovered from human B cells, therefore after different mechanisms ensuring combinatorial diversity, junctional diversity and somatic hypermutations. With such libraries, it is therefore possible to naturally generate a large variability of antibodies.

Further, these natural libraries have the advantage of using an established and validated technology and allow compatibility with various expression systems such as bacteria, yeasts, eukaryotic cells or plants.

However, generation of these libraries remains unwieldy and difficult to apply and requires resorting to a PCR (Polymerase Chain Reaction) step. For applying this PCR step, it is necessary to know the respective sequences of the 5' and 3' regions, in order to define from known germinal lines, the primers required for this PCR. If this point is not particularly bothersome for the end 3' which is located at a gene c (i.e. coding for the constant region of the antibody), it is particularly limiting as regards the end 5' which, as for it, is located at the end of the gene v, i.e. of the variability gene. This required knowledge of the region 5' of the gene v, inherently limits the selectable primers to the primers from germinal lines known up to now and therefore to the known gene v sequences. This has the effect of limiting the antibodies which may be recovered, to the antibodies having known sequences at the region 5' of their variable region, therefore setting aside all the other antibodies for which the sequences of the ends 5' of the genes v would not be known. Further, it may be necessary to modify the amino acids in the variable region in order to facilitate cloning and/or amplification.

Another drawback resulting from the required knowledge of the end 5' of the gene v, is the risk of missing the antibodies for which somatic hypermutations would have occurred at this end.

Finally, because of the PCR technique, only the antibodies for which the end 5' of the gene v will have very strong affinity with the primers used, the lower affinities not being retained, will be recovered as a priority.

The synthetic libraries, as for them, are built from different non-rearranged genes. Their rearrangement is performed in vitro by PCR and subsequently, different in vivo maturation mechanisms may be applied in order to obtain the best antibodies in terms of specificity and affinity.

By resorting to synthetic libraries, it is possible to increase the diversity of the obtained antibodies and this remains compatible with the various expression systems. However, nonetheless it is true that the work required for generating them, remains long and laborious and many drawbacks persist. Indeed, for producing synthetic libraries, a PCR step always remains mandatory. In addition to the drawbacks mentioned above, related to the use of PCR, this step requires the use of large size degenerated primers which frequently introduce deletions, additions and modifications of base pairs within the assembled v, d, j genes, which may also result in the formation of antibodies incapable of folding themselves properly and therefore non-functional. Further, the antibodies selected from these libraries are generally weakly expressed and in many cases contain mutations which may affect the immunogenicity of the antibody.

Further, with the generation of synthetic libraries, it is not possible to take into account the mutations at the junction areas ensuring junctional diversity of the somatic hypermutations. There is therefore a large loss of variability.

The present invention aims at overcoming the whole of the drawbacks listed above by describing for the first time a simple method for generating a DNA sequence coding for a heavy chain and/or a light chain, and most particularly for generating a library of antibodies having large diversity. The object of the invention is thus a method for generating a natural library of heavy chains and/or light chains of antibodies not only having its advantages but also those of a synthetic library, while getting rid of the respective drawbacks of each of the two technologies.

More particularly, the present invention differs from the whole of the techniques known up to now by doing without the PCR amplification step and consequently the whole of the drawbacks described above related to this PCR step. Most particularly, the technology, object of the present invention, no longer requires that the sequence of the end 5' of the gene v of the variable domain of the antibody be known. The present invention differs from the prior art by the amplification step which is carried out on a single strand DNA sequence. Indeed, unlike the whole of the prejudices of one skilled in the art and the state of the art limited to a standard PCR amplification step, i.e. on a double strand DNA molecule, the present invention describes for the first time a method for generating a bank of antibodies from a single primary primer and from the single strand cDNA sequence obtained from this primary primer.

According to a first aspect, the invention, object of the present patent application, is directed to a method for generating a DNA sequence coding for a heavy chain and/or a light chain of at least one antibody from an RNA extract or mixture from a cell, this cell being capable of expressing RNA coding for an antibody or at least for the heavy chain and/or the light chain of an antibody, characterized in that said method comprises at least the following steps:

a) putting a primary primer (I) in contact with said RNA extract or mixture liable to contain at least one RNA, designated here as a <<sense>> RNA, coding for the heavy chain or the light chain of an antibody, this primary primer being capable of specifically hybridizing to a fragment of the sequence of said <<sense>> RNA, comprised in the sequence coding for the constant region C of the heavy chain and/or light chain of said antibody;

b) synthesizing from said primary primer (I), a single strand cDNA designated as <<anti-sense>> cDNA;

c) eliminating if necessary, the primary primers (I) which have not hybridized in step a);

d) annealing said <<anti-sense>> cDNA by introducing a covalent bond between its end 5' and its end 3';

e) putting a secondary primer (II), designated as <<sense>> secondary primer, in contact with said <<anti-sense>> circular cDNA obtained in step d), this <<sense>> secondary primer (II) being capable of hybridizing to said <<anti-sense>> circular cDNA;

f) amplifying said <<anti-sense>> cDNA from said secondary primer (II); and g) recovering the thereby amplified <<sense>> complementary linear DNA strand.

Resorting to a PCR step requires knowledge of the sequences of the ends 5' and 3' respectively of the gene which has to be amplified in order to be able to hybridize complementary primers therein and to thereby initiate amplification by conventional techniques of the double strand molecules.

The actual principle of the invention is based on the capability of amplifying an annealed single strand DNA sequence with a suitable enzyme. It therefore clearly appears to one skilled in the art that only one complementary primer of the end 3' of the sequence which should be amplified is required. More particularly, within the scope of generating a sequence coding for an antibody, only a complementary primer of all or part of the sequence corresponding to the constant region will then become necessary for the amplification according to the invention. Once the primer is attached on the single strand DNA molecule, in the present case, the <<sense>> RNA molecule, it is sufficient to amplify the latter with a suitable enzyme capable of amplifying a single strand sequence.

One skilled in the art will easily understand that the advantage brought by the invention, object of the invention, in the sense that the latter allows entire amplification of the <<sense>> RNA sequence corresponding to the variable region, and this as far as its end 5', i.e. including if necessary, the sequences corresponding to the signal peptide as well as to the region 5'-UTR.

This aspect is particularly advantageous, in the sense that the antibody isolated by this technique may then be directly cloned with its original signal peptide, which is optimum for expressing such antibodies in a eukaryotic expression system. Indeed, without the presence of the original signal peptide, cloning of antibodies in an expression vector requires adding of a non-native signal peptide, which always requires knowledge of the sequence of the end 5' of the gene of the antibody and may introduce modifications of nucleic and/or protein sequences of such antibodies. Further, with such a method, it is possible to get rid of the whole of the drawbacks described above.

It is quite obvious that each step described above may be replaced with an equivalent step with which the essential result sought for this step may be obtained without however departing from the object of the present invention and from the desired scope of protection for this method. For the sake of clarity, it is specified here that, in the whole of the present patent application, the expressions <<sense>> and <<anti-sense>> have as system of reference, in a standard way for one skilled in the art, the 5' 3' direction of the initial RNA molecule, i.e. the RNA molecule coding for the heavy chain or the light chain of an antibody.

Accordingly, and logically, the primary primer (I) and the cDNA molecule generated from this primer, both being complementary of said RNA, are therefore characterized by the <<anti-sense>> expression. In the same way, the secondary primer (II) as well as the linear DNA molecule generated from this primer, both complementary of the generated cDNA and therefore oriented like the initial RNA sequence, will be characterized by the expression <<sense>>. Finally, in the same way, the tertiary primer (III) and the complementary DNA sequence generated form this tertiary primer will, as for them, be characterized by the expression <<anti-sense>>.

According to a preferred embodiment of the invention, the cells from which stem the extracts or mixtures of RNA are mammalian cells, preferably from mice, rats, or primates, the human origin being most preferred.

In a preferred embodiment, the RNA extract or mixture is an extract or mixture of total RNAs, an extract or mixture of RNAs enriched with messenger and/or pre-messenger RNA.

According to the second embodiment, the method, object of the invention, may be directly applied to natural, healthy cells, or cells from a pathological tissue or organ, among others a tumor, these cells being capable of expressing RNAs coding for a heavy or light chain of an antibody. The method, object of the invention, may also be applied to cells of a cell line from healthy or pathological cells.

According to an also preferred embodiment of the invention, the extracts or mixtures of RNAs originate from splenocytes, nodules or B lymphocytes.

Preferably, the cells from which stem the extracts of mixtures of RNA are B lymphocytes or one of its progenitors or a plasmocyte. Preferably, these cells are selected from pro-B progenitor cells (stem cells already engaged in B lineage), pre-B precursor cells, immature B lymphocytes, immunocompetent mature B lymphocytes or plasmocytes (see among others for the characteristics of these cells, the definitions given in the publication << Différenciation des lymphocytes B>> by Professors Marie-Paule LEERANC and Gerard LEFRANC, Université Montpellier II and Laboratoire d'ImmunoGénétique Moréculaire, LIGM, on the ImmunoGenetics site.

According to a highly preferred embodiment of the invention, the RNA extracts or mixtures stem from B lymphocytes.

According to a particular embodiment, the cells from which stem the RNAs are cells from a cell line, isolated cells from a healthy mammal or treated beforehand with a therapeutic active ingredient, among others an antigen as an immunogen, or as a vaccine, the latter may be an anti-infectious or anti-tumoral vaccine. Among these cells, it is also possible to mention cells from a patient affected with cancer or further infected by a pathogenic virus.

Thus, an advantage of the invention is to give the possibility of working starting with a large variety of cell material.

For example, according to another embodiment of the invention, it may be desired to work starting with transformed cells such as for example hybridomas resulting from fusion between B lymphocytes from spleen on the one hand and myeloma cells on the other hand.

In this application, one of the benefits of the method according to the invention, may be the possibility of obtaining the native sequence of the monoclonal antibody expressed by said hybridoma, without PCR amplification, and therefore without knowing the sequence of the 5' end of said antibody. The obtained sequence also comprises the sequence coding for the native signal peptide of said antibody and for the 5' UTR region. On this basis, the antibody may be cloned by standard means known to one skilled in the art or else, according to another embodiment, the gene corresponding to said antibody may be entirely synthesized without requiring any PCR step.

Thus, in a particular embodiment of the method according to the invention, said cell capable of expressing an antibody, is in a hybridoma.

According to a particularly preferred embodiment, the synthesis of cDNA in step b) from an RNA and a primary primer (I) is performed with any technique well-known to one skilled in the art for obtaining the synthesis of a cDNA from a primer, among others in the presence of an inverse transcriptase and a mixture of nucleotides (dNTP).

The primary primer (I) used for the synthesis of said cDNA comprises at its end 5' a group capable of being bound through a covalent bond to the end 3' of the cDNA synthesized in step b), and thereby results in the annealing of this cDNA, this group may be introduced during the synthesis of the primary primer (I). The $PO_4$ group is preferred among these groups, this group being able to form a covalent bond of the phosphodiester type with the 3' OH end of said synthesized cDNA in the presence of a DNA ligase.

In a particular embodiment, prior to the annealing step d), it is preferred to make sure that there remains no remnant of a non-hybridized primary primer (I) in the reaction medium, this in order to avoid any annealing of said primer (I) then causing amplification of said annealed primer (I) rather than the annealed cDNA of the antibody.

To do this, several solutions may be contemplated by one skilled in the art such as, as a non-limiting example, a washing of the reaction medium following the cDNA synthesis by size filtering, or with purification products of the cDNAs, being aware that the latter exclude any material below 100 base pairs (bp), or further by purification with separation on an agarose gel. According to another alternative, the amounts of primary primer (I) used will be optimized so as to be in a sub-saturating amount, step c) not being required in this configuration.

According to another preferred embodiment of the invention, said primary primer (I) is specific of a sequence located at or adjacent to the end 5' of the <<sense>> RNA sequence corresponding to the constant region C.

This aspect of the invention is advantageous in the sense that it allows synthesis and then specific amplification of the annealed cDNA of an antibody from a primer specifically recognizing at least one portion of the sequence coding for the constant region of a heavy chain or a light chain of an antibody.

In a particularly preferred embodiment, the primary primer (I) used for the synthesis of said cDNA comprises at its end 5' a group capable of being bound through a covalent bond to the end 3' of the cDNA synthesized in step b), and thereby results in the annealing of this cDNA, this group may be introduced during the synthesis of the primary primer (I). The group $PO_4$ is preferred among these groups;

this group may form a covalent bond of the phosphodiester type with the 3' OH end of said synthesized cDNA in the presence of a DNA ligase.

As the cDNA sequence is annealed, one skilled in the art will understand that the secondary primer (II) may either be specific or not, the latter amplifying in <<rolling circles>>, the entirety of the cDNA sequence will be amplified. According to an embodiment of the invention, random primers may be used.

According to a preferred embodiment of the invention, said secondary primer (II) is specific of the sequence comprised between the end 5' of said <<anti-sense>> cDNA sequence and the end 3' of the sequence of said <<anti-sense>> cDNA corresponding to the constant region C.

Even more preferably, said secondary primer (II) is specific of a sequence located at, or adjacent to, the end 5' of the <<anti-sense>> cDNA sequence.

As this will clearly be apparent from the figures, the end 5' of the <<anti-sense>> cDNA sequence also corresponds to the end 5' of the primary primer (I), the sequence of said <<anti-sense>> cDNA being of course initiated by the primary primer (I).

According to a possible embodiment of the invention, said secondary primer (II) applied in step e) of the method of the invention, consists in an <<anti-sense>> primer capable of hybridizing with the whole of the sequence coding for the primary primer (I). According to another possible embodiment, the secondary primer (II) is of a smaller size than the size of the primary primer (I) and will hybridize within the sequence coding for the primary primer (I).

More particularly, the present invention is aimed at a method characterized in that said primary (I) and secondary (II) primers each consist in a sequence of single strand DNA having a length comprised between 10 and 100 nucleotides.

Still more preferably, the method according to the invention is characterized in that said primary (I) and secondary (I) primers each respectively consist in a single strand DNA sequence with a length comprised between 20 and 60 nucleotides for the primary primer (I) and between 10 and 30 nucleotides for the secondary primer (II).

Conventionally, the synthesis of the <<anti-sense>> cDNA strand is carried out by adding free nucleotides and an enzyme of the reverse transcriptase type such as, as a non-limiting example, the reverse transcriptase Superscript III, or further the avian myeloblastosis virus or Moloney murine leukemia virus reverse transcriptase.

Preferably, the method according to the invention comprises, prior to the hybridization step a) of the primary primer (I), a step for RNA denaturation.

Denaturation of the recovered RNA may be conventionally achieved by any method known to one skilled in the art. As a non-limiting example, mention may be made of heating to 65° C. or more, of the reaction mixture, the latter allowing denaturation of any secondary structure of the RNA. The presence of the primary primer (I) in the reaction mixture during the post-denaturation cooling allows hybridization of the primary primer to its complementary sequence in said RNA with high specificity. Additionally, a protein cofactor may be added for example such as the T4 gene 32 cofactor. This allows i.a. reduction of non-specific synthesis of cDNA.

One of the key steps of the method according to the invention consists in the annealing of <<anti-sense>> cDNA. This step may be carried out with any technique known to one skilled in the art. Indeed, the possibility of getting rid of the conventional PCR steps for the amplification is based for a large part on the fact that the cDNA molecule which will be amplified in single-stranded form, is annealed. If the annealing principle of DNA is not novel as such, its application within the scope of the present invention i.e. the generation of a sequence coding for a heavy chain and/or light chain of an antibody is novel and has never been described up to now.

This annealing step may be carried out with any technique known to one skilled in the art from the moment that it allows binding through a covalent bond of the ends 5' and 3' of a same monocatenary (single-stranded) DNA.

Preferably, said annealing step is carried out by contact with a ligase of the <<ssDNA ligase>> type (<<ssDNA>> stands for <<single strand DNA>>).

According to an embodiment, the ligase is selected from CircLigase™ (Epicentre, Madison, Wis., USA) or the ssDNA thermophage or any equivalent enzyme.

However, according to a preferred embodiment of the method according to the invention, the ligase consists in CircLigase™ or any equivalent enzyme.

For more detail, one skilled in the art may refer to the following publication: (Polidoros, A. N. et al., Biotechniques 41(I), 35 (2006)).

Preferably, the ligase used introduces a covalent bond between the 3' OH end and the 5' $PO_4$ end of cDNA. To do this, a $PO_4$ group was introduced beforehand at the end 5' during the synthesis of the primary primer (I) used for the synthesis of said cDNA. Of course, any other group which may provide the same function, i.e. allow a covalent bond between the ends 5' and 3' of the cDNA molecule, may also be used.

In order to facilitate cloning of an antibody isolated through his approach, the primary primer (I) may comprise a native restriction site within the sequence of the constant portion, or even a non-native sequence specifically added thereto for facilitating this step. This added sequence as an adaptor may facilitate cloning in an expression vector. The adaptor may preferably comprise one or more restriction site(s) compatible with restriction sites present in the expression vector. A second example may consist in an adaptor comprising two DNA sequences recognized by an enzyme of the site-specific recombinase type with a restriction site between them in order to generate monomers. Said site-specific recombinase as a non-limiting example may be the lambda phage site-specific recombinase or P1 bacteriophage Cre recombinase. This adaptor may also comprise a DNA sequence comprising a restriction site for preparing the monomer with the sequences of each site adapted to <<ligase independent cloning>>.

Another key step of the method object of the invention lies in the strictly speaking amplification step of the circular <<anti-sense>> cDNA molecule. As mentioned above, this step is initiated by hybridization, in a first phase of a secondary primer (II) between the end 5' of the sequence of said <<anti-sense>> cDNA and the end 3' of the sequence corresponding to the constant region C of said same <<anti-sense>> cDNA.

This secondary primer is selected according to ways known to one skilled in the art, being aware that complementarity with cDNA sequence coding for the constant portion of one or more immunoglobulin isotype(s) and comprised between the end 5' of said constant portion and the end hybridized by the primary primer (I) is desired.

In order to amplify the cDNA molecule, the amplification step f) is applied with an enzyme capable of amplifying a single strand circular DNA sequence.

More particularly, said enzyme preferentially consists in the BSE DNA polymerase large fragment, the <<rolling circle polymerase>> of the bacteriophage φ29 or any equivalent enzyme capable of amplifying a single strand circular DNA sequence.

In a first application, direct sequencing of the amplified single strand DNA consisting in several copies of the antibody may be considered, with conventional approaches known to one skilled in the art. The sequence obtained by this approach comprises the sequences coding for the 5'-UTR region, the signal peptide and the variable portion of said antibody without it being necessary beforehand to have knowledge on the end 5' of the sequence coding for the antibody.

According to an embodiment, the method according to the invention further comprises a step for sequencing a strand of <<sense>> linear DNA recovered in step g).

This aspect is of interest, for example among others when <<anti-sense>> cDNA has been obtained from the RNA recovered from a hybridoma.

In a second application, the method object of the invention may be applied in a method for generating a bank of DNAs coding for heavy or light antibody chains, preferentially of antibodies of mammals such as mice, rats or primates, human origin being preferred.

More particularly, in this case, the object of the invention is a method for generating a bank of DNAs coding for heavy or light antibody chains, said method being characterized in that it consists of applying the method as described above, and in that it further comprises the following steps:

h) putting a tertiary primer (III), designated as an <<anti-sense>> tertiary primer, into contact with said <<sense>> linear DNA obtained in step g), this <<anti-sense>> tertiary primer (III) being capable of specifically hybridizing to a fragment of the sequence of the linear DNA comprised between the end 3' and the end 5' of said linear DNA strand and corresponding to the sequence of this linear DNA coding for the constant region C, i) generating from said tertiary primer (III), a concatemer by synthesis of a complementary <<anti-sense>> DNA strand, and j) cloning said thereby obtained double strand DNA concatemer within vectors prepared beforehand.

With such a method, it is for example possible to sequence heavy or light chains, represented by the monomers of these concatemers from the thereby obtained and cloned concatemer library.

For such a method comprised in the object of the present invention, a step for sequencing the concatemer or at least one monomer of said concatemer, will be applied at the end of step j).

By the expression of <<concatemer>>, a DNA molecule should be understood, consisting of a same repeated monomer forming a linear multimer.

More particularly, according to a preferred embodiment, said tertiary primer (III) is specific of a sequence located at, or adjacent to, the end 5' of the sequence of the <<sense>> linear DNA corresponding to the constant region C.

This aspect has the advantage of being able to synthesize a double strand complementary to the single strand concatemer and of then initiating tree amplification.

As for the primary and secondary primers, said tertiary primer (III) consists in a single strand DNA sequence having a length comprised between 10 and 100 nucleotides. A length comprised between 15 and 60 nucleotides, 15 and 50, 15 and 40, 15 and 35, and 15 and 30 for said tertiary primer (III) is even more preferred.

In a preferred embodiment, the object of the invention is a method for generating a bank of DNAs coding for heavy or light antibody chains according to the invention, characterized in that this method comprises a step prior to the cloning step j) wherein said obtained concatemer is segmented at the sequences corresponding to the primers used, this step being followed by step j) for cloning the thereby obtained double strand DNA segments within vectors prepared beforehand.

In this method for generating a bank of DNAs coding for monomers of heavy or light antibody chains, it is preferred that the primary primer (I) comprise a restriction site and that said thereby obtained concatemer be segmented at the sequence of this primary primer.

The presence of this restriction site is one of the means which may be used for segmenting the concatemer prior to step j). Because of the actual nature of the generation of the complementary strand forming the double strand concatemer, the restriction site is found on the two strands forming said concatemer. According to a first embodiment, the primary primer (I) may be selected for naturally comprising at least one restriction site. As an example, mention may be made of Hpa 1 and/or Hinc II present in the constant portion of the light chains κ or further Bgl II for the λ chains.

According to a second embodiment, the primary primer (I) may be slightly modified so as to comprise a restriction site. For example, it is possible to mutate one or two residues in order to artificially create a restriction site without however said primer losing its capability of specifically hybridizing with the desired sense RNA domain.

Finally, according to a third embodiment, the sequence coding for a restriction site may be inserted within the primary primer (I), this by preserving for said primer its capability of specifically hybridizing with the desired sense RNA domain.

The method for generating a bank of DNAs coding for monomeric segments of heavy or light antibody chains according to the invention is therefore also characterized in that said step for segmenting the concatemer is applied by enzymatic digestion with specific restriction endonucleases of the restriction site comprised or introduced into the primary primer (I).

Said monomer may then be cloned in a eukaryotic expression vector comprising the continuation of the constant portion 3' of said primary primer (I) of the heavy or light chain. Cloning may be carried out via a complementary restriction site to the one present within the primary primer (I) or by site-specific recombination. Said expression vector should comprise the elements required for expressing a recombinant protein in a host cell strain. As a non-limiting example, the vector pCEP (Invitrogen) comprises a suitable expression promoter.

More particularly, the method according to the invention is characterized in that the vector used for the step j) further comprises the sequences coding for the constant domains of the heavy or light chain of an immunoglobulin.

Preferably, said sequence coding for the constant domain of the heavy chain preferentially consists in a sequence stemming from an immunoglobulin with membrane anchoring, or comprising a transmembrane C-terminal region.

In order to facilitate screening of a bank of antibodies generated according to the invention, said sequences of heavy or light antibody chains may be cloned, for example at the end 5' of the glycosidylphosphotidylinositol binding signal sequence of a transmembrane region stemming from the human dissociation accelerating factor (decay-accelerating factor, <<DAF>> or CD55). Said thereby constructed vector should then be transfected in a eukaryotic host strain such as for example CHO, COS, HEK, NIH-3T3 cells.

Accordingly, the invention describes a method for screening a bank of cells capable of expressing a library of DNA coding for monomers of heavy or light antibody chains, said library having been generated by the method according to the invention, characterized in that it further comprises a step k) consisting of transfecting with the vector obtained in step j) of the method for generating the DNA bank according to the invention, a host cell capable of expressing the antibody coded by the double strand DNA fragment inserted within said vector, and a step 1) in which the cells expressing such DNAs coding for sequences of heavy or light antibody chains are selected.

More particularly, said host cell of step 1) consists in a cell capable of expressing at its surface the heavy chain and/or the light chain of the antibody coded by the inserted double strand DNA fragment, and even more preferentially said host cell consists in a eukaryotic cell such as for example the CHO, COS, HEK, NIH-3T3 cells.

The expression in a eukaryotic host cell has the advantage of expressing the native form of the antibody. With transfections of several cells with a mixture of cloned antibodies, it is possible to generate a bank of antibodies (or fragments comprising the heavy and/or light chain) bound or expressed at the surface of the host cell. Said banks of antibodies (or fragments) may then be screened by any approach known to one skilled in the art such as for example by separating the positive clones by FACS or by isolating polyclonal populations with an immobilized or suspended target.

According to another aspect, the use of a method according to the invention is contemplated for generating a library of antibodies or fragments thereof, comprising the heavy and/or light chain.

Similarly, the invention also covers any antibody library obtained by applying the method as described above.

Preferably, but without any limitation, the antibody library according to the invention is a library of human antibodies or fragments thereof.

According to still another aspect of the invention, any antibody, functional fragment or derived compounds obtained by screening a library obtained according to the invention, are described and claimed, said antibodies or fragments preferentially consisting in human antibodies.

Finally, according to a last aspect of the invention, an in vitro method is contemplated for screening antibodies, or their functional fragments capable of recognizing the specific epitope recognized by the antibody from which it stems, these antibodies being active against a given disease, this method comprising a step in which a blood sample is recovered from a patient suffering from said given disease and the method according to the invention is applied to said blood sample. Still more preferably, although not as a limitation, said given disease is cancer.

Other features and advantages of the invention will become apparent in the following description with the examples and the figures, the captions of which are illustrated hereafter.

CAPTION OF THE FIGURES

FIG. 4 illustrates the different primary (I), secondary (II) and tertiary (III) primers used for generating the sequence of the heavy chain in Example 2. The restriction site is underlined at the primary primer (I).

FIG. 5 illustrates the different primary (I), secondary (II), and tertiary (III) primers used for generating the sequence of the light chain in Example 2. The restriction site is underlined at the primary primer (I).

Figure 1:
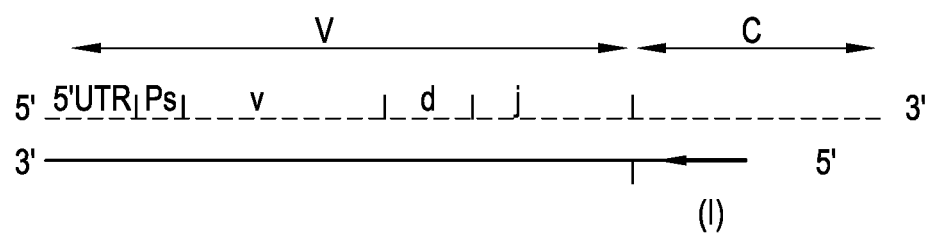
FIG. 1 is a diagram illustrating the steps a) and b) of an embodiment of the method object of the invention.

FIG. 6 illustrates the sequence obtained for the total heavy chain after sequencing (corresponding to SEQ ID NO: 11) and wherein a portion of the cloning vector (nucleic sequence in italics), the restriction site (nucleic sequence, underlined), the fragment corresponding to the primary primer I (bold-type nucleic sequence), the 5'-UTR region (boxed nucleic sequence), the signal peptide (nucleic sequence underlined twice), the variable portion of the heavy chain (bold-type amino acid sequence) and a portion of the constant part (amino acid sequence in italics), are again found.

FIG. 7 illustrates for the heavy chain, the alignments i) of the sequence of the germinal line IGHV1-18*01 in the IMGT base, ii) of the sequence of the variable domain obtained by a standard approach and iii) of the sequence of the variable domain obtained by the method object of the invention, called inventive approach in the figure, respectively.

FIG. 8 illustrates, still for the heavy chain, the alignments i) of the sequence of the signal peptide associated with the germinal line IGHV1-18*01 in IMGT base and called genomic sequence in the figure, ii) of the sequence of the signal peptide obtained by a standard approach, and iii) of the sequence of the signal peptide obtained by the method object of the invention, called inventive approach in the figure, respectively.

FIG. 9 illustrates the nucleic sequence and the protein sequence obtained for the total light chain after sequencing (corresponding to SEQ ID NO: 12) wherein the nucleic sequence underlined twice corresponds to the signal peptide, the bold-type protein sequence corresponds to the variable domain and the protein sequence in italics corresponds to the constant domain.

FIG. 10 illustrates the sequence obtained for the total heavy chain after indirect sequencing (corresponding to SEQ ID NO: 18) wherein the bold-type nucleic sequence corresponds to the primer, the underlined nucleic sequence corresponds to the restriction site Mlu I, the nucleic sequence underlined twice corresponds to the signal peptide, the bold-type protein sequence corresponds to the variable domain and the protein sequence in italics corresponds to the constant domain.

FIG. 11 illustrates the sequence obtained for the total heavy chain after combined sequencing (corresponding to SEQ ID NO: 20) wherein the nucleic sequence underlined twice corresponds to the signal peptide, the bold-type protein sequence corresponds to the variable domain, and the protein sequence in italics corresponds to the constant domain.

FIG. 12 illustrates the alignment of the sequences obtained for the total heavy chain after indirect sequencing (SEQ ID NO: 18) and combined sequencing (SEQ ID NO: 20) wherein the bold-type nucleic sequences correspond to the primary primer, the underlined nucleic sequences correspond to the restriction sites Mlu I, the sequences underlined twice correspond to the signal peptides, the bold-type protein sequences correspond to the variable domains, and the protein sequences in italics correspond to the constant domain.

Figure 13:
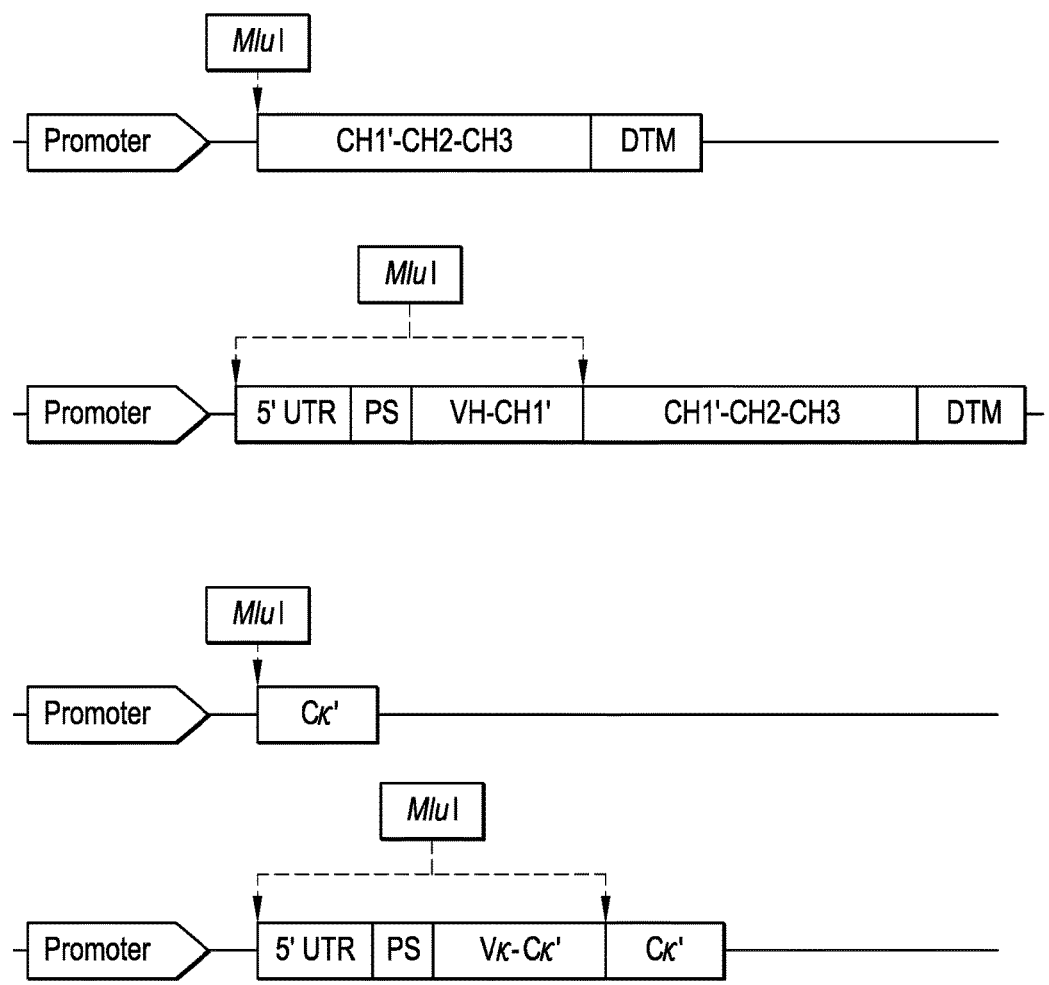

FIG. 13 illustrates a mode for cloning the variable portions of the antibodies for their presentation at the surface of the eukaryotic cells. Promoter: expression promoter i.e. CMV; Mlu I: specific restriction site for the cloning of variable portions obtained by RCA according to the invention; CH1'-CH2-CH3: partial CH1 domain and entire CH2-CH3 domain of the Fc portion of human IgG1; DTM: transmembrane domain; Cκ': partial human Cκ2 domain.

FIG. 14 illustrates the FACS analysis of the presence of antibodies at the surface of the CHO cells. Upper figure: detection of antibodies at the surface with anti-human IgG Alexa 488. Lower figure: detection of antibodies at the surface with anti-murine IgG Alexa 488. The non-expressor cells are represented by the black peak, the marked cells by the black line.

FIGS. 15A, 15B and 15C illustrate examples of primers with:

FIG. 15A: Site of the primers for cloning and sequencing human antibodies. Consensus sequence of the human IgG1-4 constant portions with addition of the restriction sites Mlu I (totally synthetic) of Mfe I (modification of a single amino acid);

FIG. 15B: Site of the primers for cloning and sequencing human antibodies. Consensus sequence of the human Iglc constant portions with addition of the restriction site Mlu I; and FIG. 15C: Site of the primers for cloning and sequencing human antibodies. Consensus sequence of the human Igk constant portions with addition of the restriction site Mlu I.

EXAMPLE 1

FIG. 1 illustrates (in dotted lines) a <<sense>> RNA strand coding for the heavy chain of an antibody, said RNA having been recovered from a hybridoma, for this example. As this has been described earlier, this RNA strand was purified. This RNA strand comprises, in the 5' 3' direction the sequence coding for the variable region as well as the sequence coding for the constant region C. More particularly, the variable region V consists of the 5'-UTR unit, of the signal peptide (Ps) as well as the v, d and j genes. Gene v corresponds to the variability gene, gene d to the diversity gene and gene j to the junction gene.

In the case of the light chain, the <<sense>> RNA strand is without any gene d. In the present patent application, only the example of the heavy chain will be described in detail, the case of the light chain being identical at the level of the different steps of the method.

An <<anti-sense>> primary primer (I) is hybridized at the constant region C. More particularly, according to a preferred embodiment illustrated here, the primary primer (I) will hybridize in proximity to the end 5' of the sequence coding for the constant region C.

As this has been described earlier, this point has a particularly interesting advantage for the invention in the sense that it is possible to make sure that during the synthesis of a cDNA strand, the integrality of the v, d and j genes will actually be preserved.

From said primary primer (I), an <<anti-sense>> cDNA strand is synthesized (illustrated as a solid line), which comprises, as for it, in the 5' 3' direction, the complementary sequences of the genes j, d and v.

The cDNA/RNA hybrid is then treated with an RNase so as to degrade the RNA strand and obtain a single strand of cDNA which may be annealed subsequently.

Figure 2:
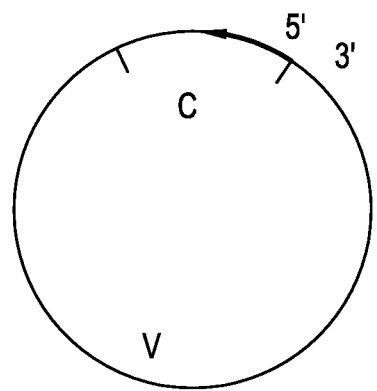
FIG. 2 is a diagram illustrating step c) of an embodiment of the method object of the invention.

The annealing step is illustrated in FIG. 2.

More particularly, the cDNA strand is illustrated, still comprising in the direction 5' 3' the sequence coding for the portion of the constant region C comprising the primer (I) and the sequence corresponding to the variable region, the latter comprising the genes j, d and v, the whole being annealed by a covalent bond between the ends 5' and 3'. To do this, as this will become apparent i.a. from the example below, the 5' end conventionally comprises a phosphate group ($PO_{4-}$) while the 3' end, as for it, comprises a hydroxyl group (OH).

Figure 3:
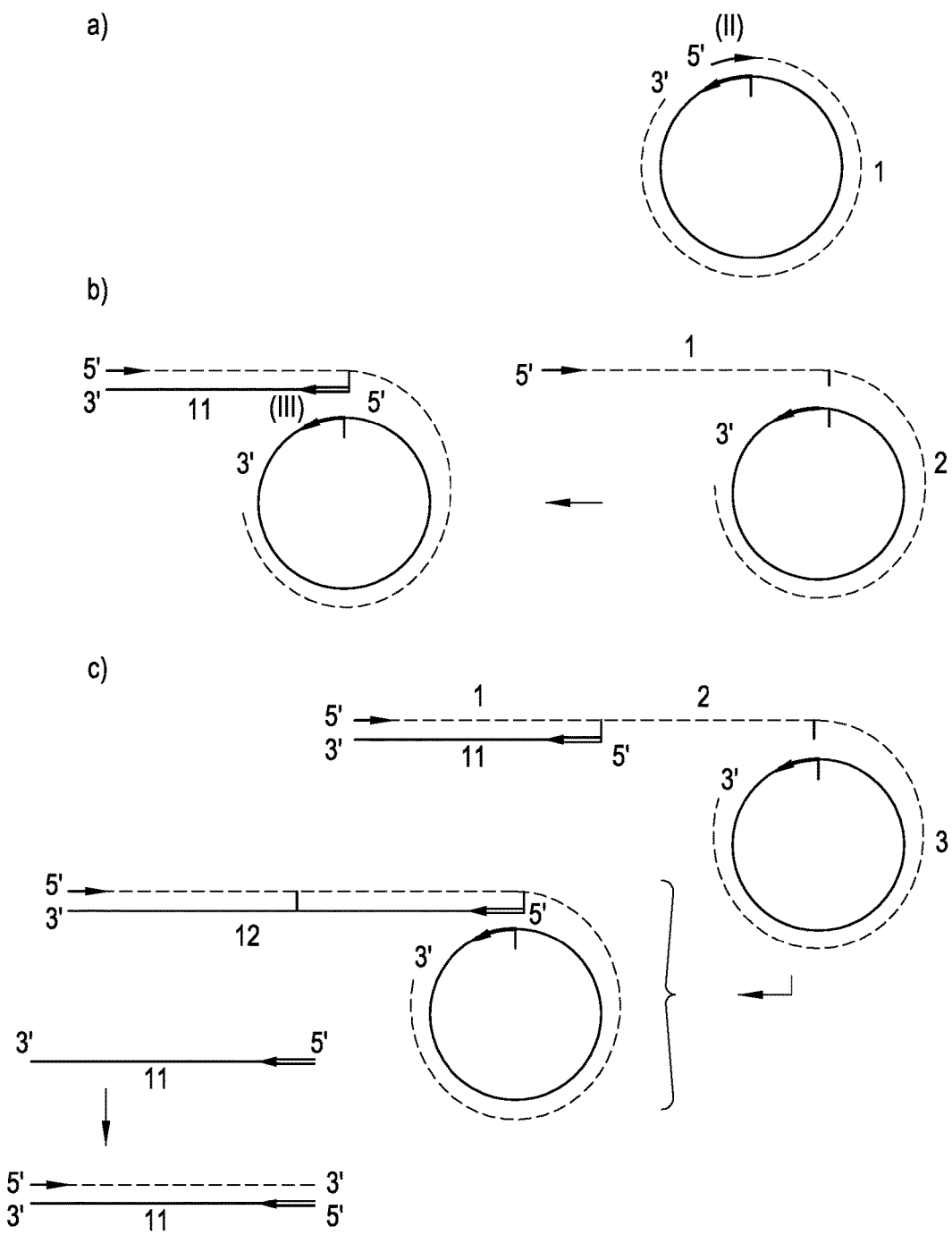
FIG. 3 is a diagram illustrating steps d), e) and f) of an embodiment of the method object of the invention.

FIG. 3 illustrates the first four amplification rounds as <<rotating circles>> or <<rolling circles>>.

FIG. 3a) represents the first amplification round. The <<sense>> secondary primer (II) hybridizes to the circular cDNA, at the sequence comprised between the end 5' of the primary primer (I) and the end 3' of the constant region C. In the embodiment illustrated here, the secondary primer (II) hybridizes at the end 5' of the primary primer (I). It is quite obvious that this hybridization position is not limiting, but is illustrated here only as an illustration. The synthesis of the complementary strand of <<sense>> DNA (illustrated in dotted lines) is then carried out by adding free nucleotides present in the reaction medium from said secondary primer (II), in the 5' 3' direction. The end of this first amplification round leads to obtaining a first unit (1) of <<sense>> DNA hybridized to the circular cDNA.

FIG. 3b) schematically illustrates the next amplification round. In the continuity of the first amplification round, a second amplification round is applied during which the free nucleotides present in the reaction medium are added at the end 3' of the first unit (1) of <<sense>> DNA thereby forming a second unit (2) of <<sense>> DNA which, during its synthesis will take the place of the first unit 1 along the circular cDNA by moving the latter. The result is a DNA molecule consisting of the second unit (2) of <<sense>> DNA hybridized to cDNA and firmly bound at its end 5' to the first unit (1) of displaced <<sense>> DNA and therefore consequently single-stranded. Simultaneously, at the moment when the first synthesized linear DNA unit (1) is displaced by the polymerase of the second unit (2), the sequence corresponding to the hybridization site of the tertiary primer (III) is released (i.e. it is single-stranded). The tertiary primer (III) will then hybridize and initiate the synthesis of a first strand of <<anti-sense>> DNA II (illustrated as a solid line) complementary to the first <<sense>> DNA unit (1).

FIG. 3c) illustrates a following round of the amplification method.

The same mechanism occurs, causing the synthesis of a third unit (3) of <<sense>> DNA along the circular cDNA, thereby displacing the <<sense>> DNA segment consisting of the first and second units (1, 2), said first unit (1) consisting in a double strand DNA because of the preceding amplification round, while the second unit (2) consists in a single strand of <<sense>> DNA. In a similar way to the preceding step, the displacement of the second unit (2) of <<sense>> DNA will release the hybridization site of the tertiary primer (III) which will bind thereto and initiate the synthesis of a second strand of complementary <<anti-sense>> DNA (12) of the second unit (2) of <<sense>> DNA. When the second newly synthesized strand of <<anti-sense>> DNA (12) will abut against the end 5' of the first strand of complementary <<anti-sense>> DNA (11) of the first unit (1), it will then assume its place along the sequence of <<sense>> DNA thereby releasing the first strand of complementary <<anti-sense>> DNA (11) of the first unit (1). The secondary primer (II) will then hybridize to the hybridization site thereby made free at the end 3' and will initiate the synthesis of the complementary strand of <<sense>> DNA along the orientation 5'3'.

FIG. 3d) illustrates the following amplification round.

Similarly, a fourth unit (4) of <<sense>> DNA is synthesized along the circular cDNA, thereby displacing the DNA segment consisting of the three first units (1, 2, 3) of <<sense>> DNA resulting from the preceding amplification rounds.

At this level of the method, the first and second units (1, 2) consist in a double strand DNA because of the preceding amplification rounds while the third unit (3) consists in a single strand of <<sense>> DNA. Similarly to the preceding step, the displacement of the third unit (3) of <<sense>> DNA will free the hybridization site of the tertiary primer (III) which will bind thereto and initiate the synthesis of a third strand of complementary <<anti-sense>> DNA (13) of the third unit (3) of <<sense>> DNA. When this third strand of newly synthesized <<anti-sense>> DNA will abut against the end 5' of the second strand of complementary <<anti-sense>> DNA (12) of the first and second units (1, 2), it will then assume its place along the sequence of <<sense>> DNA, thereby releasing said second strand of complementary <<anti-sense>> DNA (12) of the first and second units (1, 2). The secondary primer (II) may then hybridize at the hybridization site thereby made free at the end 3' of the first unit (1) or of the second unit (2), and will initiate the synthesis of a strand of complementary <<sense>> DNA of the first and second units (1, 2), along the orientation 5'3'. In the scenario when the secondary primer has hybridized at the end 3' of the second unit (2), the synthesis of a strand of complementary <<sense>> DNA has only been carried out for the second unit (2). As a result, the secondary primer (II) may subsequently hybridize at the end 3' of the first unit (1), thus initiating the synthesis of a strand of complementary <<sense>> DNA of the first and of the second units (1, 2). Now, at this second unit (2), the synthesis of the complementary strand of <<sense>> DNA will move and release the strand of <<sense>> DNA synthesized earlier. The secondary primer (II) may then hybridize to this released <<sense>> DNA strand and will initiate the synthesis of the strand of complementary <<anti-sense>> DNA (not shown).

EXAMPLE 2

Cloning and Sequencing by an <<Indirect>> Approach of the Genes of an Antibody from a Hybridoma I. Purification of the RNAs The total RNAs are isolated from $5 \times 10^6$ cells of a hybridoma concentrated beforehand by centrifugation and frozen as a pellet of cells at −80° C. The pellet of cells is thawed out and then denaturated in order to isolate the RNAs. The Mini Kit RNeasy® (Qiagen) is used for isolating the total RNAs. The purification of the total RNAs is carried out according to the instructions from the supplier. The pellet of cells is lyzed by adding 600 µL of RLT buffer containing beta-mercaptoethanol and is then homogenized by passing 6 times through a needle with a 20 gauge thickness. A volume of 600 µL of 70% ethanol is added to the homogenized lysate and then the whole is mixed by pipetting. The lysate is then applied to the RNeasy mini-column in two aliquots of 600 µL each. Centrifugation at 10,000 g for 15 seconds is carried out after each application. The RNeasy mini-column is washed with 500 µL of RPE buffer (Qiagen) and then centrifuged at 10,000 g for 15 seconds. The RNeasy mini-column is then transferred into a new microcentrifuge tube, washed with a supplement of 500 µL of RPE buffer and then centrifuged at 10,000 g for 2 minutes. The mini-column RNeasy is then placed in a new microcentrifuge tube and 50 µL of water without RNase/DNase (Ambion) are added to the column. The RNeasy mini-column is again centrifuged at 10,000 g for 1 minute. The purified total RNAs are then quantified by spectrophotometry at 260/280 nm and then immediately used for the synthesis of cDNAs.

II. Synthesis and Purification of the cDNAs

The synthesis of the cDNAs is carried out with the reverse transcription Superscript III (Invitrogen) by using the total RNAs as a template and the specific primer of the gene of the heavy chain CHssDNA (5' $PO_4$-AGC AGA CCC GGG GGC CAG TGG ATA GAC AG 3', SEQ ID NO: 1) or the specific primer of the gene of the light chain VLssDNA (5' $PO_4$-TCC AGA TGT TAA CTG CTC ACT GGA TGG TGG GAA GAT GGA TAC AG 3', SEQ ID NO: 2). The sequences of the primers are selected so as to natively comprise or allow inclusion of restriction sites by minor modifications of the parent sequence. The sequence of the primer of the heavy chain is modified so as to include the restriction site Xma I. The sequence of the primer of the light chain as for it, comprises the native restriction site Hpa I. The synthesis of the first strand of cDNA is carried out with 2.5 µg of total RNAs, 1 µL of dNTP mix (10 mM of each, Ozyme), 2 µL of specific primer of the gene (1 µM, 5' phosphorylated, Eurogentec), the whole being completed with water without DNase/RNase (Ambion) up to a total volume of 14 µL. The thereby obtained mixture is heated to 65° C. for 5 minutes and is then cooled on ice in order to allow hybridization of the primers on the template. Are then added to said mixture: 4 µL of 5×<<$1^{st}$ strand buffer>> (Invitrogen), 1 µL of DTT (1 M) and 1 µL of Superscript III (200 U/µL). The reaction mixture is then incubated at 55° C. for 1 hour and the enzymes are inactivated by heating to 70° C. for 15 minutes.

Once the synthesis of the first strand is finalized, the latter is then treated with the PCR purification kit (Qiagen) in order to eliminate the non-incorporated primers. The synthesis of cDNA is completed by adding 50 µL of water without DNase/RNase to which are added 250 µL of PB buffer (Qiagen) and the solution is mixed by pipetting. The mixture is then transferred on a PCR purification kit microcentrifuge column and is then centrifuged at 10,000 g for 1 minute. The column is washed with 750 µL of PE buffer (Qiagen) and is then centrifuged at 10,000 g for 1 minute. The column is again centrifuged at 10,000 g for 1 minute. It is then transferred into a new microcentrifuge tube of 1.5 mL and 30 µL of EB buffer (10 mM Tris-HCl pH 8.0, Qiagen) are added to the centre of the column in order to elute cDNA and the whole is then again centrifuged at 10,000 g for 1 minute. The recovered cDNA is then stored at −20° C.

Other successive steps to the cDNA synthesis such as treatment with RNase may be carried out but they are not essential.

III. Annealing of the cDNA

The single strand cDNA is annealed with the ligase CircLigase™ (Epicentre) which introduces a covalent bond between the 3' OH end and the 5' $PO_4$ end of the cDNA. The group $PO_4$ was introduced beforehand at the 5' end during the synthesis of the specific primer of the gene which was used for the synthesis of cDNA. The annealing reaction is carried out with 16 µL of purified cDNA, 2 µL of reaction buffer 10× CircLigase (Epicentre), 1 µL of ATP (1 mM), 1 µL of CircLigase (100 U/µL). The reaction is then incubated at 60° C. for 1 hour and then the enzymes are inactivated by incubation at 80° C. for 10 minutes. Following the annealing reaction, the obtained mixture is completed up to 50 μL with water without DNase/RNase to which are added 250 μL of PB buffer (Qiagen) and the solution is mixed by pipetting. The mixture is then transferred onto a PCR purification kit microcentrifuge column and centrifuged at 10,000 g for 1 minute. The column is washed with 750 μL of PE buffer (Qiagen) and is then again centrifuged at 10,000 g for 1 minute. The column is once more centrifuged at 10,000 g for 1 minute. It is then transferred in a new microcentrifuge tube of 1.5 mL and 30 μL of EB (10 mM Tris-HCl pH 8.0, Qiagen) are added to the centre of the column in order to elute the cDNA and the whole is again centrifuged at 10,000 g for 1 minute. The recovered annealed cDNA is then stored at −20° C.

IV. Amplification by <<Rotating Circle>>

The annealed single strand cDNA is amplified by using the amplification kit illustra TempliPHi™ (Amersham Biosciences) and the specific primers of the homologous gene of the sequences of primers used for the synthesis of the cDNA. The amplification reaction is conducted with 5 μL of buffer TempliPHi, 0.5 μL of annealed cDNA and 0.25 μL of sense and anti-sense primers (100 μM, Sigma ProOligo). The primers are illustrated in the Table 1 below.

chains are then cloned in the sequencing vectors pUC18 and pGEM-T, respectively. The cloned DNA inserts are then sequenced with the <<BigDye Terminator v3.1 Cycle Sequencing Kit>> (Applied Biosystems) and the primers corresponding to the sequencing vectors.

The sequence obtained after the sequencing for the total heavy chain is illustrated in FIG. 6 (SEQ ID NO 11). The portion corresponding to the variable domain, a sequence of amino acids in bold type in FIG. 6, is illustrated in the sequence SEQ ID NO: 7 while the sequence corresponding to the signal peptide, twice underlined in FIG. 6 is illustrated in the sequence SEQ ID NO: 9.

The sequence obtained after sequencing for the total light chain is illustrated in FIG. 9 (SEQ ID NO: 12). The portion of the nucleic acid corresponding to the variable domain, a sequence of amino acids in bold type in FIG. 9, is illustrated in the sequence SEQ ID NO: 13.

VI. Comparative Analysis of the Sequences of the Variable Domain and of the Signal Peptide of the Heavy Chain of the Antibody Obtained by a Standard Method and by the Approach, Subject of the Invention The standard approach for obtaining sequences of variable domains of an antibody from a hybridoma consists in

TABLE 1

|  | Heavy chain | Light chain |
| --- | --- | --- |
| Anti-sense (I) | 5'-AGCAGACCCGGGGGCAGTGGATA GACAG-3' SEQ ID NO: 1 | 5'-TCCAGATGTTAACTGCTCACTGGA TGGTGGGAAGATGGATACAG-3' SEQ ID NO: 2 |
| Sense (II) | 5'-CCACTGGCCCCCGGGTCTGC-3' SEQ ID NO: 3 | 5'-GTGAGCAGTTAACATCTGG-3' SEQ ID NO: 4 |
| Anti-sense (III) | 5'-GATAGACAGATGGGGGTGTCG-3' SEQ ID NO: 5 | 5'-GGTGGGAAGATGGATACAG-3' SEQ ID NO: 6 |

The sense and anti-sense primers are synthesized with phosphorothioate bonds so as to protect them from the exonuclease activity of the polymerase φ29. The reaction medium is heated to 95° C. for 3 minutes and then cooled on ice. A second mixture is prepared with 5 μL of reaction buffer TempliPhi and 0.2 μL of enzyme TempliPhi. Five μL of this mixture are then added to the first reaction medium prepared previously. The finalized mixture is incubated at 30° C. for 18 hours and then the enzymes are inactivated at 65° C. for minutes. The amplified double strand DNA is stored at −20° C.

V. Cloning of the Gene of the Amplified Antibody

After the amplification, the double strand DNA concatemer is digested with restriction enzymes compatible with the oligonucleotide primers used for the synthesis of the cDNA. The heavy chains of the amplified immunoglobulins are digested as follows: 7.5 μL of amplified DNA, 0.5 μL of BSA 20×, 1 μL of buffer 4 10× (NEB), 1 μL of Xma I (NEB). The mixture is incubated at 37° C. for 4 hours and then the enzymes are inactivated at 65° C. for 20 minutes. The light chains of the amplified immunoglobulins are digested as follows: 7.5 μL of amplified DNA, 0.5 μL of water, 1 μL of buffer 4 10× (NEB), 1 μL of Hpa I (NEB). The mixture is incubated at 37° C. for 4 hours. The digested heavy and light amplifying by PCR said variable domains with primers located in the signal peptide, for the sense primer, and in 5' of the constant domain CH1 for the heavy chain and Cκ for the light chain, for the anti-sense primer. It should be noted that the sense primer used usually corresponds to a degenerated sequence so as to be able to hybridize to all the possible and known assumed sequences of the signal peptides naturally used by the organism from which stems said antibody.

The sequence obtained in a standard way for the variable domain of the heavy chain is illustrated in sequence SEQ ID NO: 8.

The sequences obtained for the variable domain of the heavy chain of the exemplified antibody are then characterized by conducting immunogenetic analysis according to the IMGT nomenclature which further allows identification of the rearrangements of the different genes brought into play and a search in the database for the genomic sequence of the signal peptide associated with the genes V used during the generation of variable domains of the exemplified antibody.

Table 2 below shows the results obtained for the heavy chain.

TABLE 2

| Sequence | Gene V | % Identity | Gene J | Gene D | CDRs-IMGT | Junction VxDxJ |
| --- | --- | --- | --- | --- | --- | --- |
| Standard approach | IGHV1-18*01 | 96.88% (279/288 nt) | IGHJ2*01 | IGHD2-4*01 | [12,10,11] | CARREITTEFDYW |

TABLE 2-continued

| Sequence | Gene V % Identity | Gene J | Gene D | CDRs-IMGT | Junction VxDxJ |
|---|---|---|---|---|---|
| Inventive approach | IGHV1-18*01 96.88% (279/288 nt) | IGHJ2*01 | IGHD2-4*01 | [12,10,11] | CARREITTEFDYW |

The alignment of the sequences, illustrated in FIG. 7, as well as the immunogenetic analysis, confirm the identity existing between the sequences of the variable domain of the heavy chain obtained by the approach according to the invention (SEQ ID NO: 7) and by the standard approach (SEQ ID NO: 8).

The same approach was carried out for the sequences corresponding to the signal peptide, i.e. the sequence obtained with the method according to the invention (SEQ ID NO: 9) and obtained according to the standard approach (SEQ ID NO: 10).

By searching in the IMGT base of sequences, it is possible to obtain information relating to the identification of the gene V IGHV1-18*01 (IMGT Flat File) and to extract therefrom the nucleic and protein sequence of the signal peptide associated with the gene. In this case, the allele IGHV1-18*01 identified as the closest to the sequence of the variable domain of the heavy chain of the exemplified antibody was identified from the murine strain C57BL/6J. In the example, the murine strain used for generating the antibody is BALB/c for which the germinal line exists under the allele IGHV1-18*02. The alignment of the sequence obtained for the variable domain of the chain of the exemplified antibody shows a homology of 98.02% (248/253 nt). This homology is more significant than the one identified for the allele IGHV1-18*01 but it only concerns a shortened sequence of the gene V, i.e. 253 nt for the allele *02 in BALB/c versus 288 nt for the allele *01 in C57BL/6J. This explains while the initial analysis was favorable to the allele *01. As regards the identification of the signal peptide, it is therefore necessary to focus on the sequence again found in the murine strain used and corresponding to the allele IGHV1-18*02.

The alignment of the sequences corresponding to the signal peptide, illustrated in FIG. 8, clearly shows that the method of the present invention enables the genomic sequence (SEQ ID NO: 9) to be obtained unlike the standard approach which introduces a bias in the corresponding sequence (SEQ ID NO: 10), in this case in this example, to the modification of 4 nucleotides inducing 4 mutations at the protein sequence.

As a conclusion, this example provides confirmation that the obtained sequences actually correspond not only to the germinal lines of antibodies, but especially to the sequences obtained by standard methods. Further, this example also demonstrates the fact that the method according to the invention enables the native signal peptide to be preserved, which is modified in the standard approaches.

VII. Comparative Analysis of the Sequences of the Variable Domain and of the Signal Peptide of the Light Chain of the Antibody Obtained by a Standard Method and by the Approach Object of the Invention A similar approach was achieved and the same results (not shown) were obtained.

EXAMPLE 3

Cloning and Sequencing by an <<Indirect>> Approach of the Genes of an Antibody from a Hybridoma 1. Purification of the RNAs The total RNAs are isolated from $5 \times 10^6$ cells of a hybridoma concentrated beforehand by centrifugation and frozen as a pellet of cells at −80° C. The pellet of cells is thawed out and then denaturated in order to isolate the RNAs. The Mini Kit RNeasy® (Qiagen) is used for isolating the total RNAs. The purification of the total RNAs is carried out according to the instructions from the supplier. The pellet of cells is lyzed by adding 600 µL of RLT buffer containing beta-mercaptoethanol and is then homogenized by passing 6 times through a needle with 20 gauge thickness. A volume of 600 µL of 70% ethanol is added to the homogenized lysate and then the whole is mixed by pipetting. The lysate is then applied to the RNeasy mini-column in two aliquots of 600 µL each. Centrifugation at 10,000 g for 15 seconds is carried out after each application. The RNeasy mini-column is washed with 500 µL of RPE buffer (Qiagen) and then centrifuged at 10,000 g for 15 seconds. The RNeasy mini-column is then transferred into a new microcentrifuge tube, washed with a supplement of 500 µL of RPE buffer and then centrifuged at 10,000 g for 2 minutes. The mini-column RNeasy is then placed in a new microcentrifuge tube and 50 µL of water without RNAs/DNAs (Ambion) are added to the column. The RNeasy mini-column is again centrifuged at 10,000 g for 1 minute. The purified total RNAs are then quantified by spectrophotometry at 260/280 nm and then immediately used for the synthesis of cDNAs.

II. Synthesis and Purification of the cDNAs

The synthesis of the cDNAs is carried out with the reverse transcriptase Superscript III (Invitrogen) by using the total RNAs as a template and the specific primer of the heavy chain IGHClpO (5' $PO_4$-ACA AAC GCG TAT AGC CCT TGA CCA GGC ATC C 3', SEQ ID NO: 14) or the specific primer of the gene of the light chain IGKpO (5' $PO_4$-ACA AAC GCG TTG GTG GGA AGA TGG ATA CAG 3', SEQ ID NO: 15). The sequences of the primers comprise the restriction site Mlu I which was added at the end 5' of the native sequence. The synthesis of the first strand cDNA is achieved with 2.5 µg of total RNAs, 1 µL of DNTP mix (10 mM of each, Ozyme), 1 µL of specific primer of the gene (50 µM, phosphorylated 5', Eurogentec), the whole being completed with water without DNase/RNase (Ambion) up to a total volume of 10 µL. The thereby obtained mixture is heated to 65° C. for 5 minutes and is then cooled on ice in order to allow hybridization of the primers on the template. Are then added to said mixture: 4 µL of 5× <<Prime Script Buffer>> (Takara), 0.5 µL of Rnase inhibitor (40 U/µL), 1 µL of Prime Script RTase (200 U/μL) and the volume is then completed with 20 μL of H₂O. The reaction medium is then incubated at 50° C. for 1 hour and the enzymes are inactivated by heating to 70° C. for 15 minutes.

Once the synthesis of the first strand is finalized, the latter is then treated with the PCR purification kit (Qiagen) in order to eliminate the non-incorporated primers. The synthesis of cDNA is completed by adding 50 μL of water without DNase/RNase to which are added 250 μL of PB buffer (Qiagen) and the solution is mixed by pipetting. The mixture is then transferred on a PCR purification kit microcentrifuge column and then centrifuged at 10,000 g for 1 minute. The column is washed with 750 μL of PE buffer (Qiagen) and is then centrifuged at 10,000 g for 1 minute. The column is again centrifuged at 10,000 g for 1 minute. It is then transferred into a new microcentrifuge tube of 1.5 mL and 30 μL of EB buffer (10 mM Tris-HCl pH 8.0, Qiagen) are added to the centre of the column in order to elute the cDNA and then the whole is again centrifuged at 10,000 g for 1 minute. The recovered cDNA is then stored at −20° C.

Other successive steps to the cDNA synthesis such as the RNase treatment may be carried out but are not essential.

III. Annealing of the cDNA

The single strand cDNA is annealed with the ligase CircLigase™ (Epicentre) which introduces a covalent bond between the 3' OH end and the 5' PO₄ end of the cDNA. The group PO₄ was introduced beforehand at the 5' end during the synthesis of the specific primer of the gene which was used for the synthesis of cDNA. The annealing reaction is carried out with 1 μL of purified cDNA, 1 μL of reaction buffer 10× CircLigase (Epicentre), 1 μL of ATP (1 mM), 1 μL of CircLigase (100 U/μL) and 6 μL of H₂O. The reaction is then incubated at 60° C. for 1 hour and then the enzymes are inactivated by incubation at 80° C. for 10 minutes. Following the annealing reaction, the obtained mixture is completed up to 50 μL with water without DNase/RNase to which are added 250 μL of PB buffer (Qiagen) and the solution is mixed by pipetting. The mixture is then transferred onto a PCR purification kit microcentrifuge column and centrifuged at 10,000 g for 1 minute. The column is washed with 750 μL of PE buffer (Qiagen) and is then again centrifuged at 10,000 g for 1 minute. The column is once more centrifuged at 10,000 g for 1 minute. It is then transferred into a new microcentrifuge tube of 1.5 mL and 30 μL of EB (10 mM Tris-HCl pH 8.0, Qiagen) are added to the centre of the column in order to elute the cDNA and the whole is again centrifuged at 10,000 g for 1 minute. The recovered annealed cDNA is then stored at −20° C.

IV. Amplification by <<Rotating Circle>>

The annealed single strand cDNA is amplified by using the amplification kit illustra TempliPhi™ (Amersham Biosciences) and the specific primers of the homologous gene of the sequences of the primers used for the synthesis of cDNA. The amplification reaction is conducted with 4 μL of H₂O 0.5 μL of annealed cDNA and 0.5 μL of sense and anti-sense primers (100 μM, Sigma ProOligo). The primers are illustrated in the Table 3 below.

TABLE 3

|  | Heavy chain | Light chain |
|---|---|---|
| Anti-sense (I) | 5'-ACAAACGCGTATAGCCCTTGACCAGGCATCC-3' SEQ ID NO: 14 | 5'-CAAACGCGTTGGTGGGAAGATGGATACAG-3' SEQ ID NO: 15 |
| Sense (II) | 5'-CTAACTCCATGGTGACCCTG-3' SEQ ID NO: 16 | 5'-GGGCTGATGCTGCACCAAC-3' SEQ ID NO: 17 |
| Anti-sense (III) | 5'-GATAGACAGATGGGGGTGTCG-3' SEQ ID NO: 5 | 5'-GGTGGGAAGATGGATACAG-3' SEQ ID NO: 6 |

The sense and anti-sense primers are synthesized with phosphorothioate bonds so as to protect them from the exonuclease activity of the polymerase φ29. The reaction medium is heated to 95° C. for 3 minutes and then cooled on ice. A second mixture is prepared with 5 μL of reaction buffer TempliPhi and 0.2 μL of enzyme TempliPhi. 5 μL of this mixture are then added to the first reaction medium prepared previously. The finalized mixture is incubated at 30° C. for 18 hours and then the enzymes are inactivated at 65° C. for 10 minutes. The amplified double strand DNA is stored at −20° C.

V. Cloning of the Gene of the Amplified Antibody

After the amplification, the double strand DNA concatemer is digested with restriction enzymes compatible with the oligonucleotide primers used for the synthesis of the cDNA. The heavy chains of the amplified immunoglobulins are digested as follows: 8 μL of amplified DNA, 1 μL of buffer 3 10× (NEB), 1 μL of Mlu I (NEB). The mixture is incubated at 37° C. for 4 hours and then the enzymes are inactivated at 65° C. for 20 minutes. The light chains of the amplified immunoglobulins are digested as follows: 8 μL of amplified DNA, 1 μL of buffer 3 10× (NEB), 1 μL of Mlu I (NEB). The mixture is incubated at 37° C. for 4 hours and then the enzymes are inactivated at 65° C. for 20 minutes. The digested heavy and light chains are then respectively cloned in the sequencing vector pGEM-T. The cloned DNA inserts are then sequenced with the <<BigDye Terminator v3.1 Cycle Sequencing Kit>> (Applied Biosystems) and the primers corresponding to the sequencing vectors.

The sequence obtained after the sequencing for the total heavy chain is illustrated in FIG. 10 (SEQ ID NO: 18). The corresponding nucleic acid portion of the variable domain, a sequence of amino acids in bold type in FIG. 10, is illustrated in the sequence SEQ ID NO: 19.

EXAMPLE 4

Cloning and Sequencing by a <<Combined Approach>> of the Gene of an Antibody from a Hybridoma I. Purification of the RNAs The total RNAs are isolated from 5×10⁶ cells of a hybridoma concentrated beforehand by centrifugation and frozen as a pellet of cells at −80° C. The pellet of cells is thawed out and then denaturated in order to isolate the RNAs. The Mini Kit RNeasy® (Qiagen) is used for isolating the total RNAs. The purification of the total RNAs is carried out according to the instructions from the supplier. The pellet of cells is lyzed by adding 600 μL of RLT buffer containing beta-mercaptoethanol and is then homogenized by passing 6 times through a needle with 20 gauge thickness. A volume of 600 μL of 70% ethanol is added to the homogenized lysate and then the whole is mixed by pipetting. The lysate is then applied to the RNeasy mini-column in two aliquots of 600 μL each. Centrifugation at 10,000 g for 15 seconds is carried out after each application. The RNeasy mini-column is washed with 500 μL of RPE buffer (Qiagen) and then centrifuged at 10,000 g for 15 seconds. The RNeasy mini-column is then transferred into a new microcentrifuge tube, washed with a supplement of 500 μL of RPE buffer and then centrifuged at 10,000 g for 2 minutes. The mini-column RNeasy is then placed in a new microcentrifuge tube and 50 μL of water without RNase/DNase (Ambion) are added to the column. The RNeasy mini-column is again centrifuged at 10,000 g for 1 minute. The purified total RNAs are then quantified by spectrophotometry at 260/280 nm and then immediately used for the synthesis of cDNAs.

II. Synthesis Purification of the cDNAs

The synthesis of the cDNAs is carried out with the reverse transcriptase Superscript III (Invitrogen) by using the total RNAs as a template and the specific primer of the heavy chain IGHClpO (5' $PO_4$— ACA AAC GCG TAT AGC CCT TGA CCA GGC ATC C 3', SEQ ID NO: 14) or the specific primer of the gene of the light chain IGKpO (5' $PO_4$— ACA AAC GCG TTG GTG GGA AGA TGG ATA CAG 3', SEQ ID NO: 15). The sequences of the primers are selected so as to natively comprise or allow inclusion of restriction sites with minor modifications of the parent sequence. The sequences of the primers of the heavy and light chain are modified so as to include the restriction site Mlu I at the end 5'. The synthesis of the first strand of cDNA is achieved with 2.5 μg of total RNAs, 1 μL of DNTP mix (10 mM of each, Ozyme), 2 μL of specific primer of the gene (50 μM, phosphorylated 5', Eurogentec), the whole being completed with water without DNase/RNase (Ambion) up to a total volume of 14 μL. The thereby obtained mixture is heated to 65° C. for 5 minutes and is then cooled on ice in order to allow hybridization of the primers on the template. Are then added to said mixture: 4 μL of 5× <<$1^{st}$ strand buffer>> (Invitrogen), 1 μL of DTT, and 1 μL of Superscript III (200 U/μL). The reaction medium is then incubated at 50° C. for 1 hour and the enzymes are inactivated by heating to 70° C. for 15 minutes.

Once the synthesis of the first strand is finalized, the latter is then treated with the PCR purification kit (Qiagen) in order to eliminate the non-incorporated primers. The synthesis of cDNA is completed by adding 50 μL of water without DNase/RNase to which are added 250 μL of PB buffer (Qiagen) and the solution is mixed by pipetting. The mixture is then transferred onto a PCR purification kit microcentrifuge column and then centrifuged at 10,000 g for 1 minute. The column is washed with 750 μL of PE buffer (Qiagen) and then is centrifuged at 10,000 g for 1 minute. The column is again centrifuged at 10,000 g for 1 minute. It is then transferred in a new microcentrifuge tube of 1.5 mL and 30 μL of EB buffer (10 mM Tris-HCl pH 8.0, Qiagen) are added to the centre of the column in order to elute the cDNA and then the whole is again centrifuged at 10,000 g for 1 minute. The recovered cDNA is then stored at −20° C.

Other successive steps to the cDNA synthesis such as the RNase treatment may be carried out but are not essential.

III. Annealing of the cDNA

The single strand cDNA is annealed with the ligase CircLigase™ (Epicentre) which introduces a covalent bond between the 3' OH end and the 5' $PO_4$ end of the cDNA. The group $PO_4$ was introduced beforehand at the 5' end during the synthesis of the specific primer of the gene which was used for the synthesis of cDNA. The annealing reaction is carried out with 16 μL of purified cDNA, 2 μL of reaction buffer 10× CircLigase (Epicentre), 1 μL of ATP (1 mM), 1 μL of CircLigase (100 U/μL). The reaction is then incubated at 60° C. for 1 hour and then the enzymes are inactivated by incubation at 80° C. for 10 minutes. Following the annealing reaction, the obtained mixture is completed up to 50 μL with water without DNase/RNase to which are added 250 μL of PB buffer (Qiagen) and the solution is mixed by pipetting. The mixture is then transferred onto a PCR purification kit microcentrifuge column and centrifuged at 10,000 g for 1 minute. The column is washed with 750 μL of PE buffer (Qiagen) and is then again centrifuged at 10,000 g for 1 minute. The column is once more centrifuged at 10,000 g for 1 minute. It is then transferred in a new microcentrifuge tube of 1.5 mL and 30 μL of EB (10 mM Tris-HCl pH 8.0, Qiagen) are added to the centre of the column in order to elute the cDNA and the whole is again centrifuged at 10,000 g for 1 minute. The recovered annealed cDNA is then stored at −20° C.

IV. Amplification by <<Rotating Circle>>

The annealed single strand cDNA is amplified by using the amplification kit illustra TempliPhi™ (Amersham Biosciences) and the specific primers of the homologous gene of the sequences of the primers used for the synthesis of cDNA. The amplification reaction is conducted with 5 μL of water, 0.5 μL of annealed cDNA and 0.5 μL of sense and anti-sense primers (100 μM, Sigma ProOligo). As the primers are identical with those of Example 3 above, they are illustrated in Table 3.

The sense and anti-sense primers are synthesized with phosphorothioate bonds so as to protect them from the exonuclease activity of the polymerase φ29. The reaction medium is heated to 95° C. for 3 minutes and then cooled on ice. A second mixture is prepared with 5 μL of reaction buffer TempliPhi and 0.2 μL of enzyme TempliPhi. Five μL of this mixture are then added to the first reaction medium prepared beforehand. The finalized mixture is incubated at 30° C. for 18 hours and then the enzymes are inactivated at 65° C. for 10 minutes. The amplified double strand DNA is stored at −20° C.

The heavy chains of the amplified immunoglobulins are digested as follows: 8 μL of amplified DNA, 1 μL of buffer 3 10× (NEB), 1 μL of Mlu I (NEB). The mixture is incubated at 37° C. for 4 hours and then the enzymes are inactivated at 65° C. for 20 minutes. The light chains of the amplified immunoglobulins are digested as follows: 8 μL of amplified DNA, 1 μL of buffer 3 10× (NEB), 1 μL of Mlu I (NEB). The mixture is incubated at 37° C. for 4 hours and then the enzymes are inactivated at 65° C. for 20 minutes. The monomers of the heavy chain are separated by electrophoresis on agarose gel (1% w/v) at 10V/cm. The DNA corresponding to the monomers is then extracted and isolated with the Nucleospin Extract II kit (Machery Nagel) according to the procedure of the manufacturer with elution in 15 μL of <<elution buffer>>. The DNA is then sequenced with the <<BigDye Terminator v3.1 Cycle Sequencing Kit>> (Applied Biosystems) by using the primary or tertiary primer according to the cDNA synthesis and by <<rotating circle>> amplification under the following conditions: 5 μL of monomeric DNA, 2 μL of 5× Buffer (Applied Biosystems), 2 μL of BigDye Terminator v3.1, 1 μL of primer (10 μM). The conditions of the reaction follow the programming of the machine Fast Thermal Cycler 9800 (Applied Biosystems), program <<BigDye std>>.

The sequence obtained after the sequencing for the total heavy chain is illustrated in FIG. 11 (SEQ ID NO: 20). The nucleic acid portion corresponding to the variable domain, a sequence of amino acids in bold type in FIG. 11, is illustrated in the sequence SEQ ID NO: 21.

EXAMPLE 5

Comparison of the Sequences Obtained by an <<Indirect>> Approach and by a <<Combined Approach>>

In order to validate the different alternatives of the invention, i.e. the indirect approach and the combined approach (also called direct approach), an alignment of the sequences obtained for the total heavy chains was carried out with both approaches respectively.

FIG. 12 illustrates this alignment.

As this is clearly apparent from this figure, the obtained sequences are identical, which validates both approaches of the present invention.

EXAMPLE 6

Detection of the Expression at the Surface of the Eukaryotic Cells

In order to carry out screening of the antibodies cloned according to the invention, a eukaryotic expression vector was modified so as to contain a transmembrane domain (DTM) at the C-terminal end of the constant portion of the heavy chains of a human antibody. The DTM was cloned in cis with the constant domain of a human heavy chain of the IfG1 type (FIG. 13) so that the antibodies expressed in the host cells no longer have to be expressed in the culture supernatant but are retained at the surface of the cells. With cloning by restriction with Mlu I and ligation in the vector containing the DTM, it is possible to insert the variable portions comprising their 5'UTR portion and the signal peptide in cis with the constant domain, the light chains are cloned in the same way in a vector without DTM (FIG. 13). The variable portions of the heavy and light chains of a murine antibody are cloned in the expression vectors in cis with the human constant domains: IgG1 (heavy chain) or Igk (light chain), with DTM for the heavy chain. Next, co-transfection of the host CHO cells with the expression vectors of the heavy and light chain was then carried out by transfection with lipofectamine. After a growth time of 48 hrs in a growth medium with serum, the cells were washed with PBS.

The presence of the antibodies on the surface of the cells washed beforehand, was detected by incubation of the cells with IgG anti-human or IgG anti-mouse antibodies. The IgG anti-human or anti-mouse antibodies, marked beforehand with the fluorophor ALEXA 488 (Molecular Probes, A11013), enable identification of the cells which bear the antibodies at the membrane surface of the host cells. By flow cytometry analysis, it is then possible to detect the cells bearing the antibodies at the surface relatively to the host cells without any expression vector (FIG. 14). The chimeric nature of the antibodies, murine variable portions and human constant portions, enables detection with the IgG anti-human or IgG anti-mouse antibodies.

EXAMPLE 7

List of the Different Murine and Human Primers which may be Used Within the Scope of Application of the Invention The present example lists, in a non-limiting way, sequences of preferred primers for applying the invention.

I. Murine primers

TABLE 4

Primary primers (I) for the synthesis of specific murine cDNA for each isotype of the constant domains in Balb/c mice. The restriction site Mlu I is underlined and in italics.

| Primers | Sequence |
|---------|----------|
| IGHC1pO | ACAA_ACGCGT_ATAGCCCTTGACCAGGCATCC (SEQ ID NO: 14) |
| IGHC2ApO | ACAA_ACGCGT_ATAACCCTTGACCAGGCATCC (SEQ ID NO: 22) |
| IGHC2BpO | ACAA_ACGCGT_CAGGGATCCAGAGTTCCAAG (SEQ ID NO: 23) |
| IGHC3pO | ACAA_ACGCGT_GTAGCCTTTGACAAGGCATCC (SEQ ID NO: 24) |
| IGKpO | ACAA_ACGCGT_TGGTGGGAAGATGGATACAG (SEQ ID NO: 15) |

TABLE 5

Secondary primers (II) for amplification of the annealed cDNA. The 3' bonds are phosphothioate (*) instead of phosphodiester.

| Primers | Sequence |
|---------|----------|
| IgCHISPT | CTAACTCCATGGTGACCC*T*G (SEQ ID NO: 16) |
| IgCH2aSPT | ACTGGCTCCTCGGTGAC*T*C (SEQ ID NO: 25) |
| IgCH2bSPT | AGTGACTGTGACTTGGAAC*T*C (SEQ ID NO: 26) |
| IgCH2bSbisPT | GTCTATCCACTGGCCCC*T*G (SEQ ID NO: 27) |
| IgCH3SPT | CTGGATCCTCGGTGACAC*T*G (SEQ ID NO: 28) |
| IgCKSPT | GGGCTGATGCTGCACCA*A*C (SEQ ID NO: 17) |

TABLE 6

Tertiary primers (III) for amplification of the annealed cDNA. The 3' bonds are phosphothioate (*) instead of phosphodiester.

| Primers | Sequence |
|---------|----------|
| IgCH1ASPT | GATAGACAGATGGGGGTGT*C*G (SEQ ID NO: 5) |
| IgCH2aASPT | GATAGACCGATGGGGC*T*G (SEQ ID NO: 29) |

TABLE 6-continued

Tertiary primers (III) for amplification of the annealed cDNA. The 3' bonds are phosphothioate (*) instead of phosphodiester.

| Primers | Sequence |
| --- | --- |
| IgCH2bASPT | GATAGACTGATGGGGGTGT*T*G (SEQ ID NO: 30) |
| IgCH3ASPT | GATAGACAGATGGGGC*T*G (SEQ ID NO: 31) |
| IgCKASPT | CAGTTGGTGCAGCATCA*G*C (SEQ ID NO: 41) |

II. Human Primers

TABLE 7

Primary primers (I) for the synthesis of specific human cDNA for any isotype IgG. The restriction site Mlu I is underlined and in italics.

| Primers | Sequence |
| --- | --- |
| HuCH1pO | ACGCGTTTGACCAGGCAGCCCAGG (SEQ ID NO: 32) |
| HuCκpO | ACGCGTCAGATTTCAACTGCTCATCAGATGG (SEQ ID NO: 33) |
| HuCλpO | ACGCGTAGTGTGGCCTTGTTGGCTTG (SEQ ID NO: 34) |

TABLE 8

Secondary primers (II) for amplification of the annealed cDNA. The 3' bonds are phosphothioate (*) instead of phosphodiester.

| Primers | Sequence |
| --- | --- |
| HuCH1SPT | GCCCTGGGCTGCCTGG*T*C (SEQ ID NO: 35) |
| HuCκSPT | CATCTGATGAGCAGTTGAAATCT*G*G (SEQ ID. NO: 36) |
| HuCλSPT | CAAGCCAACAAGGCCAC*A*C (SEQ ID NO: 37) |

TABLE 9

Tertiary primers (III) for amplification of the annealed cDNA. The 3' bonds are phosphothioate (*) instead of phosphodiester.

| Primers | Sequence |
| --- | --- |
| HuCH1SPT | GATGGGCCCTTGGT*G*G (SEQ ID NO: 38) |
| HuCκASPT | GGAAGATGAAGACAGATGGT*G*C (SEQ ID NO: 39) |
| HuCλASPT | GGAGGGYGGGAACAGAGTG* A* C (SEQ ID NO: 40) |

FIGS. 15A, 15B and 15C also illustrate the different primers and corresponding sites.

The invention claimed is:

1. A method for generating a bank of DNAs coding for at least one heavy chain or a light chain of at least one antibody from an extract or mixture of RNA from a cell, characterized in that it applies a method for generating a DNA sequence coding for a heavy chain or a light chain of at least one antibody from an extract or mixture of RNA from a cell by converting RNA into said DNA sequence, characterized in that said method comprises at least the following steps:

a) generating two primers, primary primer (I) and secondary primer (II), wherein primary primer (I) is complementary to any region of any RNA that codes for a heavy or light chain of any region C of any antibody and wherein secondary primer (II) has reverse complementarity to any region of primer (I);
   b) putting a primary primer (I) in contact with said RNA extract or mixture liable to contain at least one RNA, designated here as a sense RNA, coding for the heavy chain or the light chain of an antibody, this primary primer specifically hybridizing to a fragment of the sequence of said sense RNA, this fragment being comprised in the sequence coding for the constant region C of the heavy or light chain of said antibody;
   c) synthesizing, from said primary primer (I), a single strand cDNA designated as anti-sense cDNA;
   d) eliminating if necessary, the primary primer (I) which have not hybridized to the fragment of the sequence of said RNA in step a);
   e) annealing said anti-sense cDNA by forming a covalent bond between its ends 5' and 3' to form an anti-sense circular cDNA;
   f) putting a secondary primer (II), designated as sense secondary primer, in contact with said anti-sense circular cDNA obtained in step e), this sense secondary primer (II) hybridizing to said anti-sense circular cDNA;
   g) amplifying said anti-sense cDNA from said secondary primer (II), wherein said amplification is applied with an enzyme that amplifies a sequence of single strand circular DNA, wherein said enzyme consists in the rolling circle polymerase of the bacteriophage φ29; and
   h) recovering the thereby amplified sense complementary linear DNA strand, wherein the recovered amplified sense complementary linear DNA strand codes for a heavy chain or a light chain of at least one antibody from an extract or mixture of the RNA from a cell, wherein said amplification step is carried out on a single strand sequence,
   i) putting a tertiary primer (III), designated as anti-sense tertiary primer, into contact with said sense linear DNA obtained in step h), this anti-sense tertiary primer (III) specifically hybridizes to a fragment of the sequence of the linear DNA comprised between the end 3' and the end 5' of said linear DNA strand and corresponding to the sequence of this linear DNA coding for the constant region C,
   j) generating from said tertiary primer (III), a concatemer by synthesis of a complementary anti-sense DNA strand, and
   k) cloning said thereby obtained double strand DNA concatemer into a vector.

2. The method according to claim 1, characterized in that said tertiary primer (III) is specific of a sequence located at or adjacent to the end 5' of the sequence of the sense linear DNA corresponding to the constant region C.

3. The method for generating a bank of DNAs coding for heavy or light antibody chains according to claim 1, characterized in that it comprises, prior to step k), a step consisting of segmenting the concatemer at the sequences corresponding to the primers used.

4. The method according to claim 3, characterized in that the primary primer (I) comprises a restriction site.

5. The method according to claim 3, characterized in that said step k) for segmenting the concatemer is applied by enzymatic digestion with a specific restriction endonuclease of the restriction site comprised in the primary primer (I).

6. The method according to anyone of claim 1, characterized in that the vector used for step k) further comprises sequences coding for the constant domains of the heavy or light chain of an immunoglobulin.

7. The method according to claim 6, characterized in that said sequence coding for the constant domain of the heavy chain preferentially consists in a sequence from an immunoglobulin with membrane anchoring, or comprising a transmembrane C-terminal region.

8. The method according to claim 1, characterized in that it further comprises a step l) for transfecting with the vector obtained in step k) a host cell that expresses the heavy or light chain of the antibody coded by the double strand DNA fragment inserted within said vector.

9. The method according to claim 8, characterized in that said host cell of step l) is a cell that expresses at its surface the antibody coded by the inserted double strand DNA fragment.

10. The method according to claim 9, characterized in that said host cell is an eukaryotic cell.

11. The method according to claim 10, characterized in that said eukaryotic cell is selected from CHO, COS, HEK and NIH-3T3 cells.

12. The method according to claim 1, characterized in that the cells from which stem the extract or mixture of RNA are of human origin.

* * * * *